United States Patent
Davidson

(10) Patent No.: US 12,400,755 B2
(45) Date of Patent: Aug. 26, 2025

(54) VIRTUAL SIGNAGE USING AUGMENTED REALITY OR MIXED REALITY

(71) Applicant: Hill-Rom Services, Inc., Batesville, IN (US)

(72) Inventor: Frederick Collin Davidson, Apex, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 433 days.

(21) Appl. No.: 17/555,644

(22) Filed: Dec. 20, 2021

(65) Prior Publication Data
US 2022/0208367 A1    Jun. 30, 2022

Related U.S. Application Data

(60) Provisional application No. 63/132,660, filed on Dec. 31, 2020.

(51) Int. Cl.
| | |
|---|---|
| *G16H 40/63* | (2018.01) |
| *A61B 90/00* | (2016.01) |
| *A61B 90/90* | (2016.01) |
| *G16H 10/60* | (2018.01) |

(52) U.S. Cl.
CPC ............. *G16H 40/63* (2018.01); *A61B 90/36* (2016.02); *A61B 90/90* (2016.02); *G16H 10/60* (2018.01); *A61B 2090/365* (2016.02)

(58) Field of Classification Search
CPC ........ G16H 40/63; G16H 10/60; G16H 40/20; G16H 40/67; A61B 90/36; A61B 90/90; A61B 2090/365; A61B 2017/00216
See application file for complete search history.

(56) References Cited

U.S. PATENT DOCUMENTS

| | | |
|---|---|---|
| 10,037,821 B2 | 7/2018 | Johnson et al. |
| 10,642,046 B2 | 5/2020 | Kaul et al. |
| 2014/0081659 A1* | 3/2014 | Nawana ................. G16H 10/20 705/3 |
| 2014/0145915 A1 | 5/2014 | Ribble et al. |

(Continued)

OTHER PUBLICATIONS

Medgadget, Augmented Reality Hospital Market Share, Current Trends and Research Development Report to 2025, Jun. 9, 2020, Brandessence market Research and Consulting Pvt. Ltd., 7 pages.

(Continued)

*Primary Examiner* — Kee M Tung
*Assistant Examiner* — Khoa Vu
(74) *Attorney, Agent, or Firm* — Price Heneveld LLP

(57) ABSTRACT

An information system for displaying virtual signage in a medical facility includes a treatment device. A visual identifier is operably coupled to the treatment device. A controller is configured to communicate with a remote device having an image sensor for sensing the visual identifier within a field of detection. The controller is configured to recognize the visual identifier sensed by the remote device, determine device information associated with the visual identifier based on a configuration of the visual identifier, retrieve the device information relating to the treatment device associated with the visual identifier from an information source, and generate a virtual image including the device information configured to be viewed via the remote device.

20 Claims, 13 Drawing Sheets

(56) References Cited

U.S. PATENT DOCUMENTS

| | | | |
|---|---|---|---|
| 2015/0363566 A1* | 12/2015 | Johnson | G16H 20/30 |
| | | | 705/3 |
| 2018/0197624 A1 | 7/2018 | Robaina et al. | |
| 2018/0369039 A1* | 12/2018 | Bhimavarapu | A61G 7/018 |
| 2019/0197055 A1 | 6/2019 | Rodriguez et al. | |
| 2019/0333213 A1 | 10/2019 | Boettger et al. | |
| 2019/0336085 A1* | 11/2019 | Kayser | A61B 5/202 |
| 2022/0391617 A1* | 12/2022 | Chastain | G06V 10/95 |
| 2023/0075466 A1* | 3/2023 | Robaina | A61B 3/113 |
| 2023/0410998 A1* | 12/2023 | Durlach | A61G 7/0528 |

OTHER PUBLICATIONS

Uzun, Vassilya and Bilgin, Sami, Evaluation and implementation of QR Code Identity Tag system for Healthcare in Turkey, SpringerPlus (2016)5:1454, 24 pages.

Yaskevich, Anastasia, Science Soft, How Augmented Reality Can Help Doctors and Patients, Health IT Outcomes, Guest Column, Apr. 24, 2018, 3 pages.

Kim, Mi Jeong; Wang, Xiangyu; Han, Sooyeon; and Wang, Ying; Implementing an augmented reality-enabled wayfinding system through studying user experience and requirements in complex environments; Visualization in Engineering a SpringerOpen Journal; Kim et al. Visualization in Engineering (2015) 3:14; 12 pages.

Scanning and Detecting 3D Objects, Apple Developer Documentation; Sample Code; https://developer.apple.com/documentation/arkit/scanning_and_detecting_3d_objects; Nov. 12, 2020; 6 pages.

* cited by examiner

VIRTUAL SIGNAGE USING AUGMENTED REALITY OR MIXED REALITY

CROSS-REFERENCE TO RELATED APPLICATION

This application claims priority to U.S. Provisional Patent Application No. 63/132,660, filed on Dec. 31, 2020, entitled "VIRTUAL SIGNAGE USING AUGMENTED REALITY OR MIXED REALITY," the disclosure to which is hereby incorporated herein by reference in its entirety.

FIELD OF THE DISCLOSURE

The present disclosure generally relates to virtual signage, and more particularly to virtual signage at a medical facility utilizing augmented reality or mixed reality.

SUMMARY OF THE DISCLOSURE

According to one aspect of the present disclosure, an information system for displaying virtual signage in a medical facility includes a treatment device. A visual identifier is operably coupled to the treatment device. A controller is configured to communicate with a remote device having a sensor for sensing the visual identifier within a field of detection. The controller is configured to recognize the visual identifier sensed by the remote device, determine device information associated with the visual identifier based on a configuration of the visual identifier, retrieve the device information relating to the treatment device associated with the visual identifier from an information source, and generate a virtual image including the device information configured to be viewed via the remote device.

According to another aspect of the present disclosure, an information system for a medical facility in which visual identifiers are associated with the medical facility where the information system includes a query member associated with each visual identifier. The query member is at least one of a patient identification feature, a treatment device, and a room environment. A controller is configured to communicate with a remote device and a server. The controller is configured to recognize the visual identifiers sensed by the remote device, associate the visual identifiers with information related to at least one of a patient, the treatment device, and the room environment based on the query member, retrieve the information from an information source, and generate a virtual image including the information to be communicated to a user via the remote device.

According to yet another aspect of the present disclosure, a method of displaying information to a caregiver, including sensing a visual identifier positioned within a field of detection of a sensor of a remote device via at least one of an imager and an environmental sensor; recognizing the visual identifier; retrieving information relating to at least one of a room environment, a patient, and a treatment device based on the configuration of the visual identifier; generating a virtual image including the information; and displaying the virtual image via at least one of a display of the remote device and within a field of view of a user of the remote device.

These and other features, advantages, and objects of the present disclosure will be further understood and appreciated by those skilled in the art by reference to the following specification, claims, and appended drawings.

DETAILED DESCRIPTION

Figure 1:
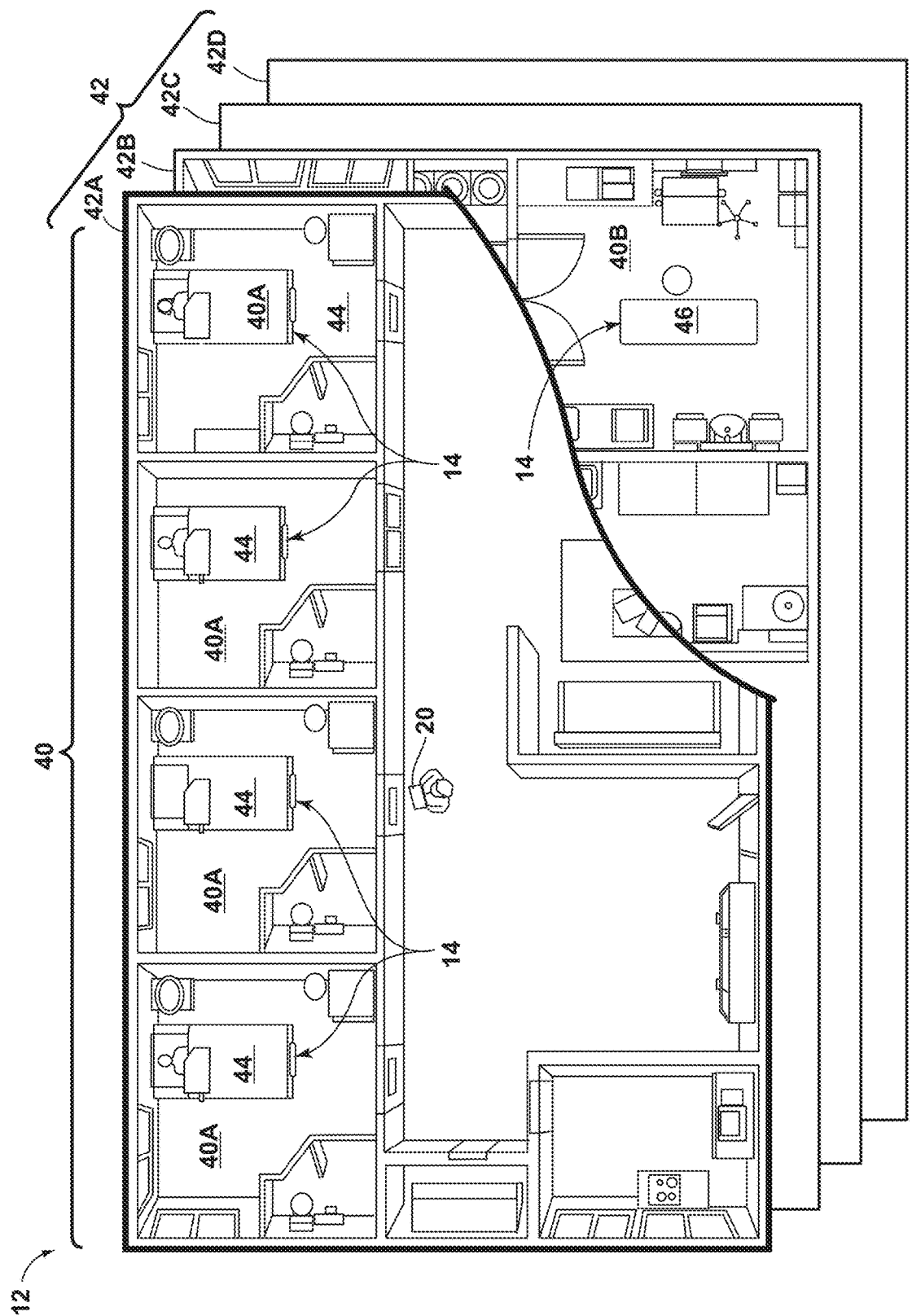
FIG. 1 is a schematic diagram of a portion of a medical facility having an information system of the present disclosure.

The present illustrated embodiments reside primarily in combinations of method steps and apparatus components related to virtual signage using augmented reality or mixed reality. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof, shall relate to the disclosure as oriented in FIG. 1. Unless stated otherwise, the term "front" shall refer to a surface closest to an intended viewer, and the term "rear" shall refer to a surface furthest from the intended viewer. However, it is to be understood that the disclosure may assume various alternative orientations, except where expressly specified to the contrary. It is also to be understood that the specific structures and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

Referring to FIGS. 1-14, reference numeral 10 generally designates an information system for a medical facility 12 that includes a treatment device 14. A data tag, such as a visual identifier 16, is operably coupled to the treatment device 14. The controller 18 is configured to communicate with a remote device 20 having a sensor 22 for sensing the visual identifier 16 within a field of detection 24. The controller 18 is configured to recognize the visual identifier 16 sensed by the remote device 20. The controller 18 is configured to determine device information 26 associated with the visual identifier 16 based on a configuration of the visual identifier 16 and retrieve the device information 26 relating to the treatment device 14 associated with the visual identifier 16 from an information source 28. Additionally, the controller 18 is configured to generate a virtual image 30 that includes the device information 26, which is viewable via the remote device 20.

The information system 10 is configured to retrieve information from one or more information sources 28 to present the information to a caregiver or another user. Each visual identifier 16 has a specific and unique configuration, which allows the controller 18 to recognize the visual identifier 16. Based on the configuration of the visual identifier 16, the controller 18 is configured to determine what information to retrieve and from where the information is to be retrieved. Further, each visual identifier 16 is associated with a specific query member 36. Each query member 36 is an item, space, person, device, etc. that the caregiver is seeking information about. In various examples, the query members 36 are the treatment device 14, a patient identification feature 38 worn by a patient, and a room environment 40 of the medical facility 12. Each query member 36 has a specific data tag or visual identifier 16 with a specific configuration, which allows the information system 10 to determine the information to be obtained for the caregiver.

Referring to FIG. 1, the medical facility 12 includes multiple room environments 40, such as patient rooms 40A, surgical suites 40B, imaging areas, waiting rooms, etc. on a number of floors 42, illustrated as floors 42A-42D. Each room environment 40 includes at least one treatment device 14 for treating or otherwise caring for a patient. In the configuration illustrated in FIG. 1, the treatment devices 14 include a medical bed 44 within each patient room 40A and a surgical table 46 in the surgical suite 40B. The treatment devices 14 may communicate the device information 26, as well as patient information 48, to the information system 10, as discussed further herein.

Figure 2:
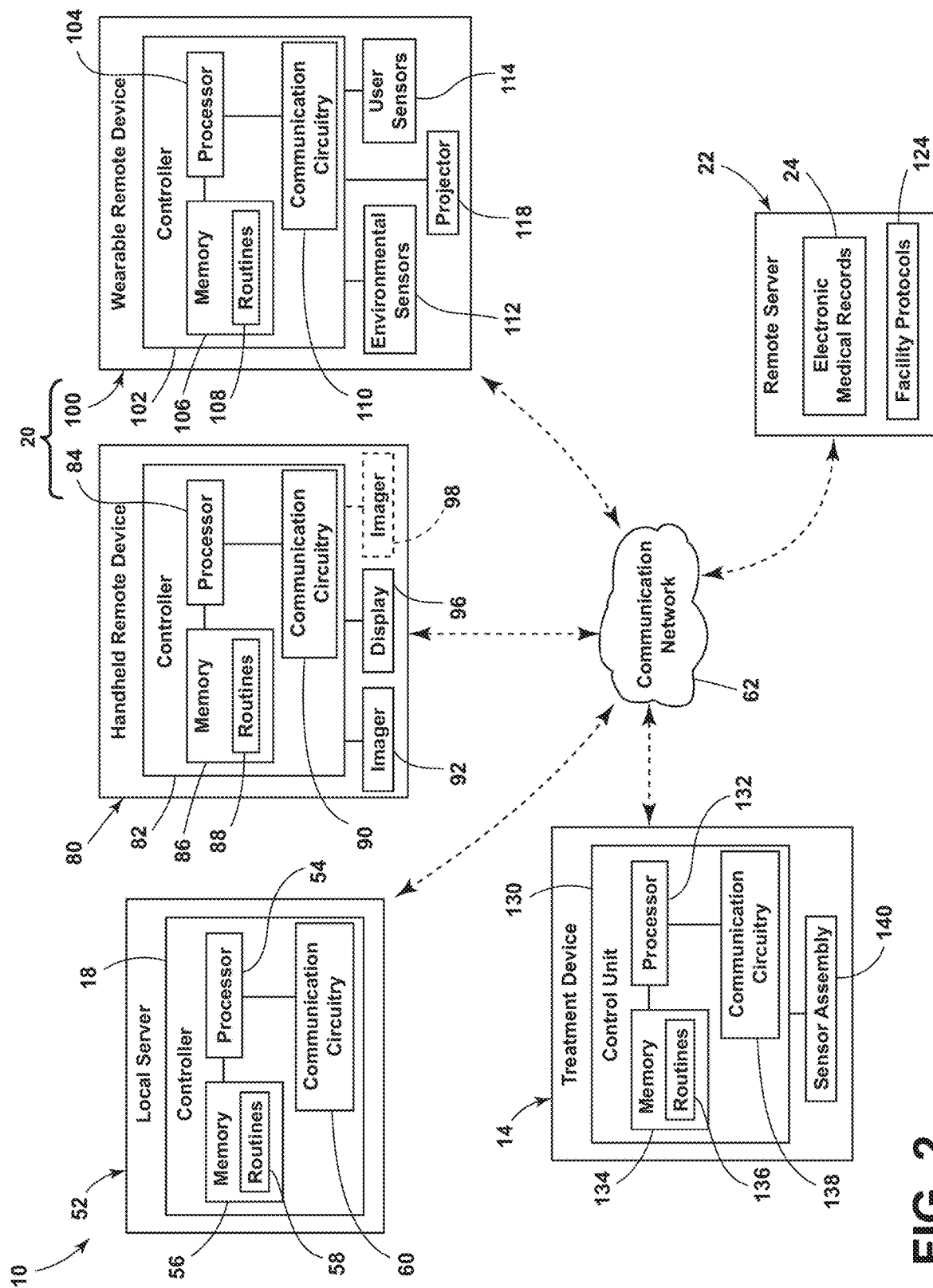
FIG. 2 is a block diagram of an information system for a medical facility, according to the present disclosure.

Referring to FIG. 1, as well as FIG. 2, the information system 10 provides a caregiver with more convenient and efficient access to the device information 26 (FIG. 11) and the patient information 48 (FIG. 9), as well as other confidential or private information useful for caring for the patient. Traditionally, the device information 26 and the patient information 48 are included in hardware or handwritten notes and charts, which can be cumbersome, expensive, and have potential privacy concerns. The information system 10 for the medical facility 12 disclosed herein utilizes the remote device 20 to display virtual signage that may include the device information 26, the patient information 48, any additional information useful for the caregiver, or a combination thereof.

The virtual signage (e.g., the virtual image 30) is displayed using at least one of augmented reality and mixed reality. The use of augmented reality or mixed reality provides a convenient and efficient method for accessing information stored in a variety of locations or systems while maintaining the confidentiality of the information. Additionally, the use of augmented reality or mixed reality restricts access to the information to those caregivers and other medical professionals with authorized access to the information.

The remote device 20 may have a variety of configurations that may determine whether augmented reality or mixed reality is utilized to view the information. Augmented reality overlays virtual objects on a real-world environment to enhance the real-world environment. Generally, the real-world environment includes captured image data and the virtual objects are overlaid on the captured data so a user can view both the real-world environment and the virtual objects together on a display or device. The user interacts with the real-world environment while digital or virtual content is added.

In comparison, mixed reality goes beyond augmented reality and allows the user to interact with the virtual objects. The virtual objects are overlaid on the real-world environment; however, the virtual objects respond and react to the user as a real object would as set forth in further detail herein. Generally, the virtual objects are projected into the real-world environment that the user views using a wearable device or display. The information system 10 may use one or both of augmented reality and mixed reality to display information to the caregiver, as discussed further herein.

Referring still to FIG. 2, the controller 18 of the information system 10 may be included at least partially in a local server 50 of the medical facility 12, a remote server 52, or a combination thereof. The controller 18 includes a processor 54, a memory 56, and other control circuitry. Instructions or routines 58 are stored within the memory 56 and executable by the processor 54. The control circuitry may also include communication circuitry 60 to permit communication via a communication network 62 or various protocols for wireless communication in combination with a wired network, as discussed further herein. Additionally, the routines 58 may include operating instructions to enable the various processes and methods described herein.

Figure 3:
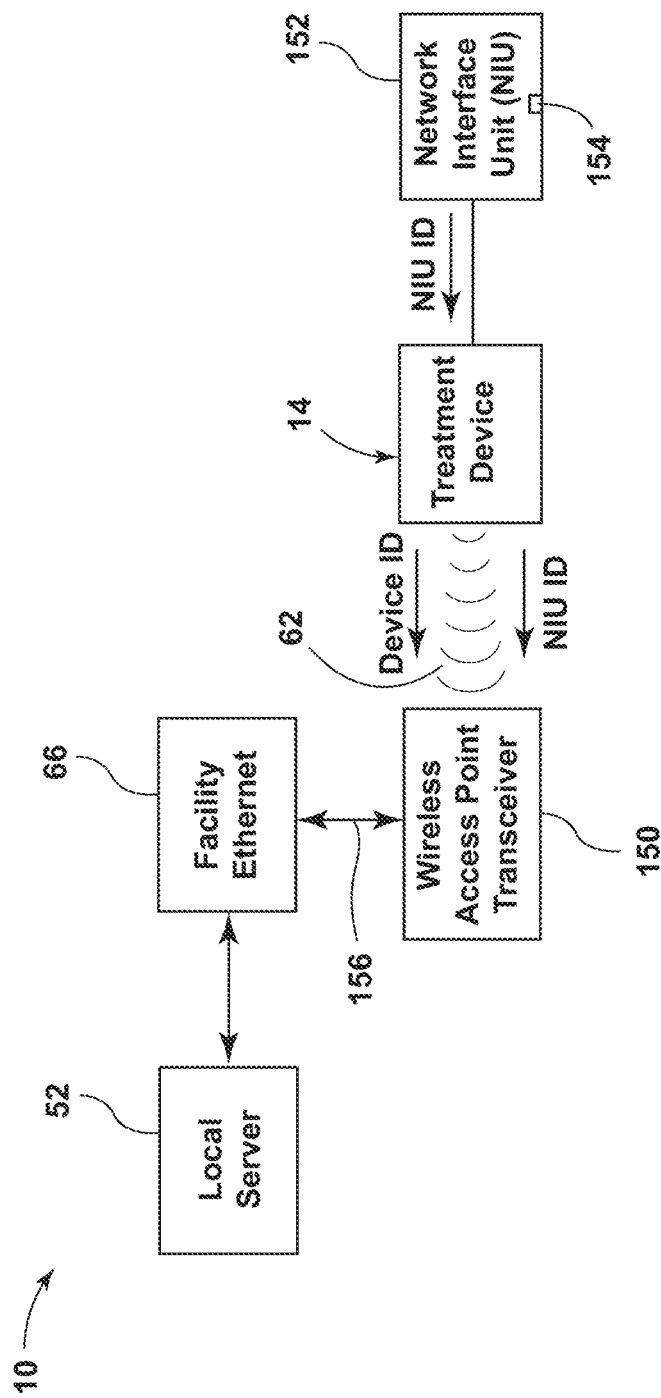
FIG. 3 is a block diagram of an information system with a treatment device in wireless communication with a server, according to the present disclosure.

The local server 50 is in communication with at least one of the remote device 20, the treatment device 14, and the remote server 52 via the communication network 62. The communication network 62 may be part of an overall facility network of the medical facility 12. The facility network may include a combination of wired connections (e.g., Ethernet 66, as illustrated in FIG. 3) as well as wireless networks, which may include the wireless communication network 62. The communication network 62 may include a variety of electronic devices, which are configured to communicate over various wired or wireless communication protocols.

In the illustrated configuration of FIG. 2, the local server 50 is in wireless communication with the treatment devices 14, the remote device 20, and the remote server 52. The communication network 62 may include a wireless router through which the remotely accessed treatment devices 14 and the remote device 20 may be in communication with one another, as well as the local server 50 or the remote server 52 via the network.

The communication network 62 may be implemented via one or more direct or indirect, non-hierarchical communication protocols, including, but not limited to, Bluetooth®, Bluetooth® low energy (BLE), Thread, Ultra-Wideband, Z-Wave, ZigBee®, etc. Additionally, the communication network 62 may correspond to a centralized or hierarchal communication network 62 where one or more of the treatment devices 14 or the remote device 20 communicate via the wireless router (e.g., a communication routing controller). Accordingly, the communication network 62 may be implemented in a variety of communication protocols in various combinations, including, but not limited to global system for mobile communication (GSM), general packet radio services, code division multiple access, enhanced state GSM environment, fourth generation (4G) wireless, fifth generation (5G) wireless, Wi-Fi, world interoperability for microwave access (WiMAX), local area network (LAN), Ethernet 66, etc. By flexibly implementing the communication network 62, the various treatment devices 14 and the remote device 20 may be in communication with one another and the remote server 52 directly via the wireless communication network 62 or via a cellular data connection.

Referring still to FIG. 2, the remote device 20 may be configured as a handheld device 80. The handheld device 80 may be a phone, a laptop, a tablet, or other portable handheld devices 80 associated with the medical facility 12 or the caregiver. In certain aspects, the handheld device 80 may be a personal caregiver device, such as a personal phone, which is convenient or efficient for the caregiver as the caregiver conducts rounds between the various patient rooms 40A (FIG. 1).

The handheld device 80 includes a control unit 82 having a processor 84, a memory 86, and other control circuitry. Instructions or routines 88 are stored within the memory 86 and executable by the processor 84. The handheld device 80 may include communication circuitry 90 for communicating with at least one of the local server 50, the remote server 52, and the treatment devices 14 through the communication network 62. The control circuitry may also include image processing circuitry for processing image data captured by the handheld device 80.

Figure 8:
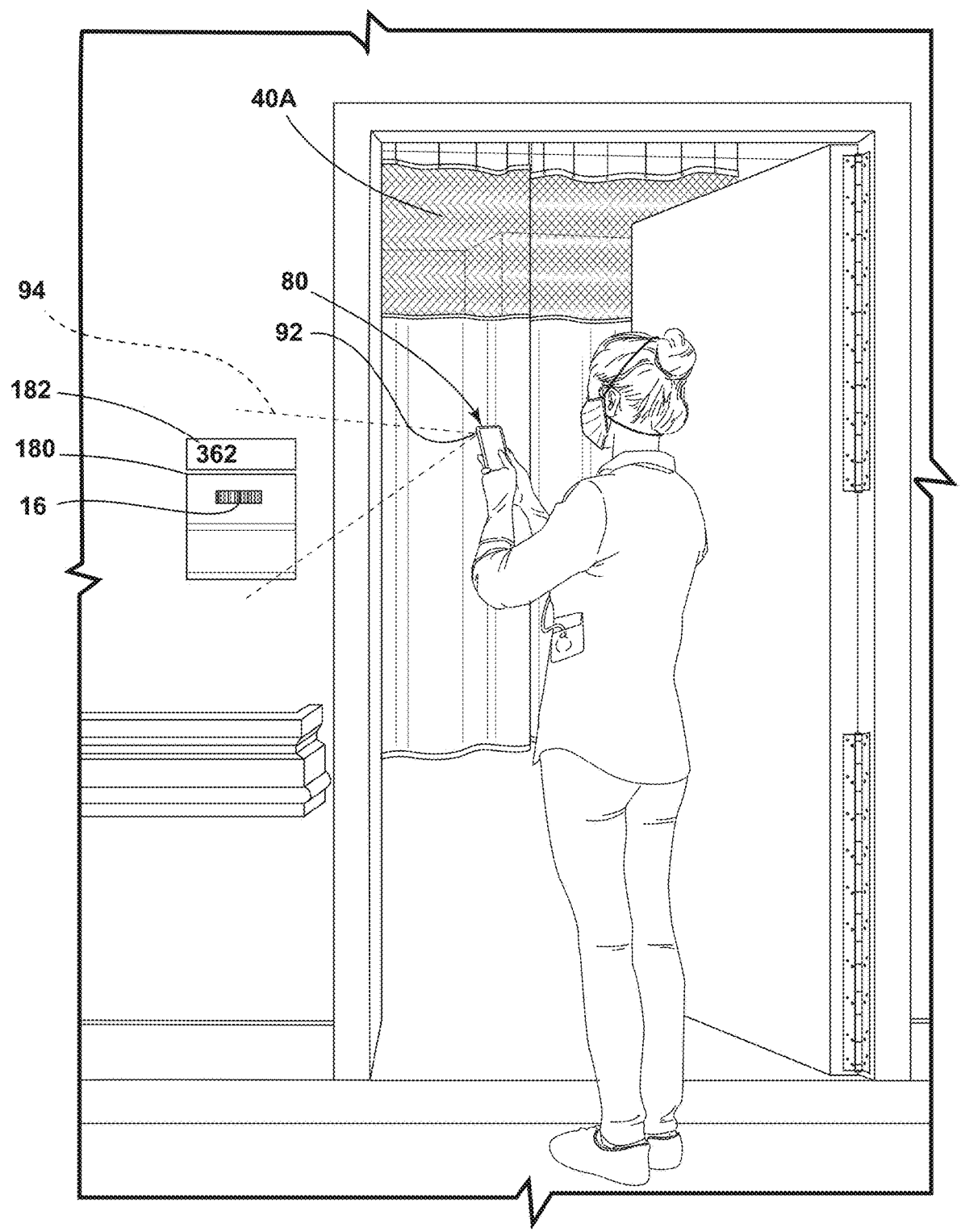
FIG. 8 is a schematic view of a caregiver using a remote device to recognize a visual identifier on a room plaque, according to the present disclosure.

The handheld device 80 generally includes the sensor 22 configured as an imager 92, also referred to as an image sensor, defining the field of detection 24 (FIG. 8). The imager 92 is generally a forward facing imager or camera on a backside of the handheld device 80 relative to a display 96. The handheld device 80 may also include an additional image sensor or imager 98, which may be rearward (e.g., on an opposing side relative to the display 96) or forward facing (e.g., on a same side as the display 96) depending on the configuration of the handheld device 80. The imagers 92, 98 may each be any practicable type of image-based sensor, such as a charge coupled device, a metal oxide semiconductor imager, or any type of color or black-and-white camera. The imager 92 captures data from the field of detection 24, while the imager 98 captures image data within a separate field of detection. The data captured by the imagers 92, 98 generally includes image data, such as at least one of a picture, video, real-time streaming of data, other transmissions of image data, or combinations thereof. The image data may be a single image or multiple images.

The imagers 92, 98 may be adjustable, which may also adjust the field of detection 24 to be broader, narrower, positionally shifted, or any combination thereof. The imagers 92, 98 may receive a signal from the controller 18 based on the data or a user input to adjust an aspect of the imagers 92, 98. For example, the imager 92 may be adjusted to change the scope of the field of detection 24. It is contemplated that each imager 92, 98 includes one or more lenses, which may be adjusted to change the sharpness or quality of the data obtained by the imagers 92, 98, respectively. Generally, the imager 92 captures image data relating to the visual identifier 16 (FIG. 8), which is then communicated to the controller 18 to retrieve the information associated with the visual identifier 16. The associated information is then conveyed to the caregiver via the display 96 of the handheld device 80 using augmented reality. The additional imager 98 may be utilized for facial recognition of the caregiver for providing access to the information as described further herein.

Additionally or alternatively, the remote device 20 may be configured as a wearable device 100. Generally, the wearable device 100 is configured as glasses or another head-mounted display. The wearable device 100 includes a control unit 102 that has a processor 104, a memory 106, and other control circuitry. Instructions or routines 108 are stored within the memory 106 and executable by the processor 104. The wearable device 100 includes communication circuitry 110 for communicating via the communication network 62. The control circuitry may also be configured to process sensed information obtained by the wearable device 100.

The wearable device 100 may be utilized to display information using augmented reality and/or mixed reality. The wearable device 100 may display information via augmented reality in a similar manner as discussed in relation to the handheld device 80. To utilize mixed reality, the wearable device 100 includes the sensor 22 configured as environmental sensors 112 for sensing a variety of environmental information in the surrounding environment of the caregiver. The environmental sensors 112 each define the field of detection 24, respectively, that extends from the wearable device 100 and away from the caregiver. The environmental sensors 112 sense the presence of objects within the surrounding environment, the position and distance to the objects, the depth of the object, lighting information, a combination thereof, etc.

For example, the environmental sensors 112 may include infrared cameras or Light Detection and Ranging (LIDAR) emitters and detectors to capture depth or range in the surrounding environment. The environmental sensors 112 may also include multiple sensors, such as an infrared sensor or Red, Green, Blue (RGB) cameras that sense information about the movement of the user, such as the position, orientation, and motion of the user within the environment. Further, the environmental sensors 112 may sense the interaction of the caregiver with the sensed objects and/or with the virtual image 30.

The wearable device 100 also includes the sensor 22 configured as user sensors 114, which are generally configured to monitor or sense additional information about the user (e.g., the caregiver). The user sensors 114 may include an inertial-movement unit that monitors the movement of the head of the caregiver. Additionally or alternatively, the user sensors 114 may include eye-tracking sensors to track the position and movement of eyes of the caregiver. The eye-tracking sensors may track a focus of the caregiver (e.g., a focus direction) and define a field of view 116 (FIG. 10) of the caregiver corresponding with a line of sight into the surrounding environment.

The direction of the focus of the caregiver may be determined by measuring an eye-ellipse of the caregiver. The eye-ellipse is a graphical device that represents the approximation of the eye location distribution of the caregiver as a multidimensional normal density distribution. The eye-ellipse results in a set of lines that isolate an ellipse area, which may account for about 90% of eye positions. The direction of focus of the caregiver may be utilized by the information system 10 to display or project the virtual image 30 using mixed reality through a projector 118 of the wearable device 100. Further, the user sensors 114 may include at least one gesture sensor to track position, movement, and gestures of the caregiver, which may determine the interaction of the caregiver with the virtual image 30.

Referring still to FIG. 2, the remote device 20 conveys information to the caregiver. The controller 18 retrieves the information from various information sources 28 including multiple locations and systems. The information sources 28 may include the local server 50, the remote server 52, an electronic medical record 120, a caregiver interaction system 122, a nurse call system 124, other systems of the medical facility 12, or a combination thereof. For example, the controller 18 is in communication with remote server 52 to obtain the patient information 48 from the electronic medical record 120 and/or to obtain facility protocols 126. Additionally or alternatively, the electronic medical records 120, the facility protocols 126, or a combination thereof may be stored on the local server 50.

The electronic medical record 120 may be associated with the patient and include current and historical information relating to demographics, allergies, infections, treatments, medications, medical history, etc. of the patient. The caregiver interaction system 122 may include information communicated between caregivers, recent updates, shared data, etc. that may or may not be ultimately stored in the electronic medical record 120. Additionally, the nurse call system 124 may include communication between the patient and the caregiver including, number of calls, type of calls, substance of calls, etc. The information and software for the various systems may be stored on the local server 50, the remote server 52, the handheld device 80 (such as the personal caregiver device), or a combination thereof. The controller 18 communicates with the handheld device 80, the remote server 52, and/or the local server 50 to retrieve information associated with the patient to subsequently convey to the caregiver via the remote device 20.

Additionally or alternatively, in the illustrated example of FIG. 2, the remote server 52 stores the facility protocols 126, which may relate to, for example, safety features, treatment processes, device protocols, etc. The facility protocols 126 may determine or contribute to the information communicated to the caregiver. For example, if a certain safety protocol is not initiated but should be initiated based on the patient information 48, the information conveyed to the caregiver may prompt activation of the safety protocol.

The information system 10 also retrieves the device information 26 and/or the patient information 48 from the treatment device 14. Generally, a variety of treatment devices 14 may be utilized for treating and caring for the patient while the patient is at the medical facility 12. Each treatment device 14 includes a control unit 130 that has a processor 132, a memory 134, and other control circuitry. Instructions or routines 136 are stored within the memory 134 and executable by the processor 132. The treatment device 14 generally includes a sensor assembly 140 configured to sense information about the patient to be communicated to the information system 10.

Each treatment device 14 may include communication circuitry 138 for communicating via the communication network 62. The information system 10 may communicate directly with the treatment device 14 without communicating through the communication network 62. Additionally or alternatively, the treatment device 14 may communicate with the local server 50, and the information system 10 may obtain the information from the local server 50.

Figure 4:
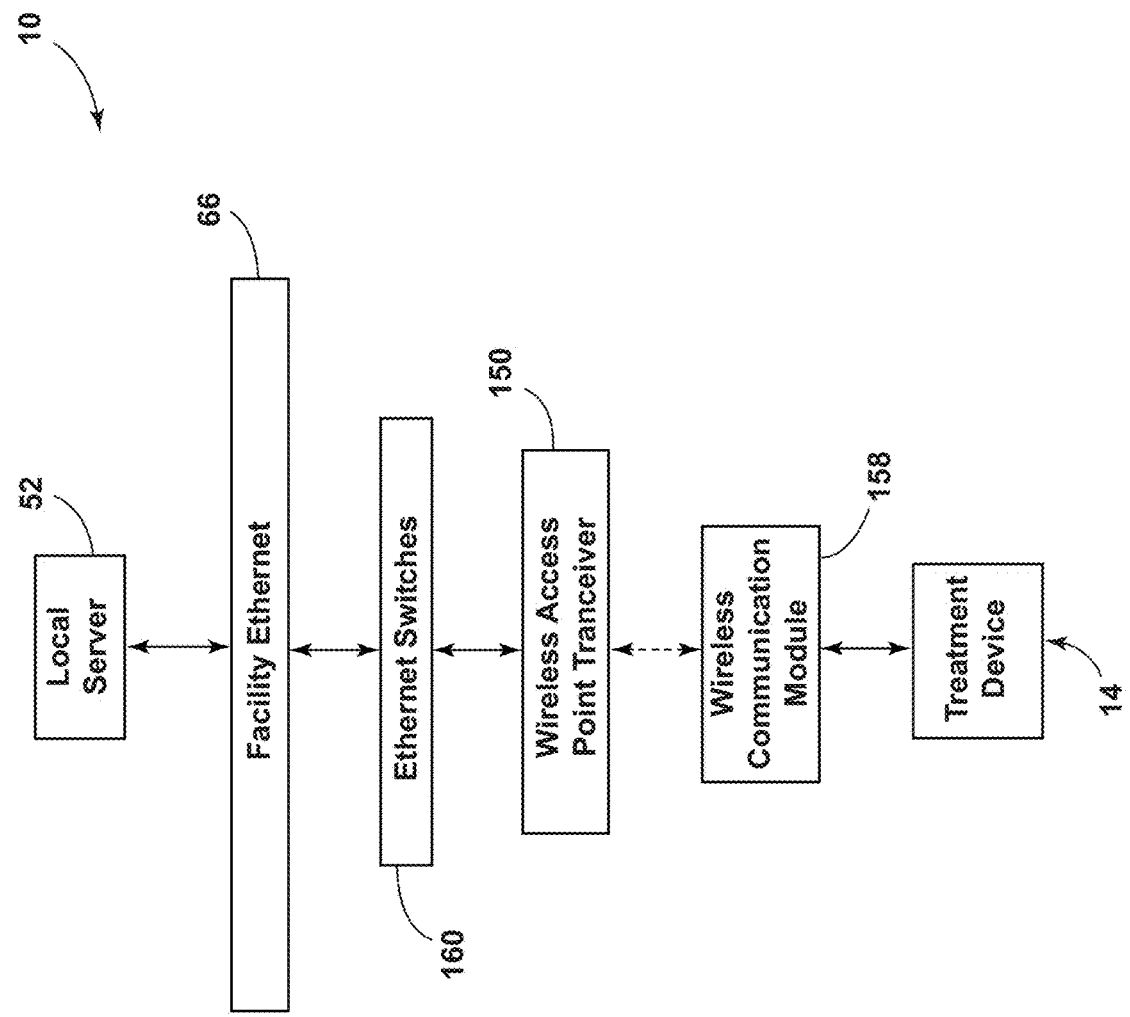
FIG. 4 is a block diagram of an information system with a treatment device in wireless communication with a server, according to the present disclosure.

Referring to FIGS. 3 and 4, exemplary configurations of the communication between the treatment device 14 and the local server 50 are illustrated. For example, as illustrated in FIG. 3, the treatment device 14 may be configured to communicate with a wireless access point transceiver 150, which is coupled to Ethernet 66 of the medical facility 12. The communication network 62 provides for bidirectional communication between the treatment device 14 and the wireless access point transceiver 150. The treatment device 14 is associated with a network interface unit 152. Multiple network interface units 152 may be provided in various locations of the medical facility 12.

Each treatment device 14 and each network interface unit 152 is assigned a unique identification (ID) code, such as a serial number. Various components of the information system 10 (e.g. the local server 50, the remote device 20, etc.) may include software (e.g. routines 58, 108, 136) that operate to associate the ID of the treatment device 14 with the network interface unit ID data to locate each treatment device 14 within the medical facility 12. Each network interface unit 152 includes a port 154 for selectively coupling with Ethernet 66. When the network interface unit 152 is coupled with Ethernet 66, the network interface unit 152 communicates ID data to treatment device 14, which then wirelessly communicates ID data for the treatment device 14 and the network interface unit 152 to the wireless access point transceiver 150. The wireless access point transceiver 150 communicates bidirectionally with Ethernet 66 via a data link 156. The local server 50 is in communication with Ethernet 66 to receive the data or information from the treatment device 14.

Additionally or alternatively, as illustrated in FIG. 4, the treatment device 14 may be capable of communicating wirelessly via a wireless communication module 158. The wireless communication module 158 generally communicates via an SPI link with circuitry of the associated treatment device 14 (e.g., the communication circuitry 138) via a wireless 802.11b link and the wireless access point transceiver 150. Multiple wireless access point transceivers 150 may be also located throughout the medical facility 12. The wireless access point transceivers 150 are generally coupled to Ethernet switches 160 via 802.3 links. It is contemplated that the wireless communication modules 158 may communicate with the wireless access point transceivers 150 via any of the wireless protocols disclosed herein. Additionally or alternatively, the Ethernet switches 160 generally communicate with Ethernet 66 via an 802.3 link, and Ethernet 66 is also in communication with the local server 50, allowing information and data to be communicated between the local server 50 and the treatment device 14.

Figure 6:
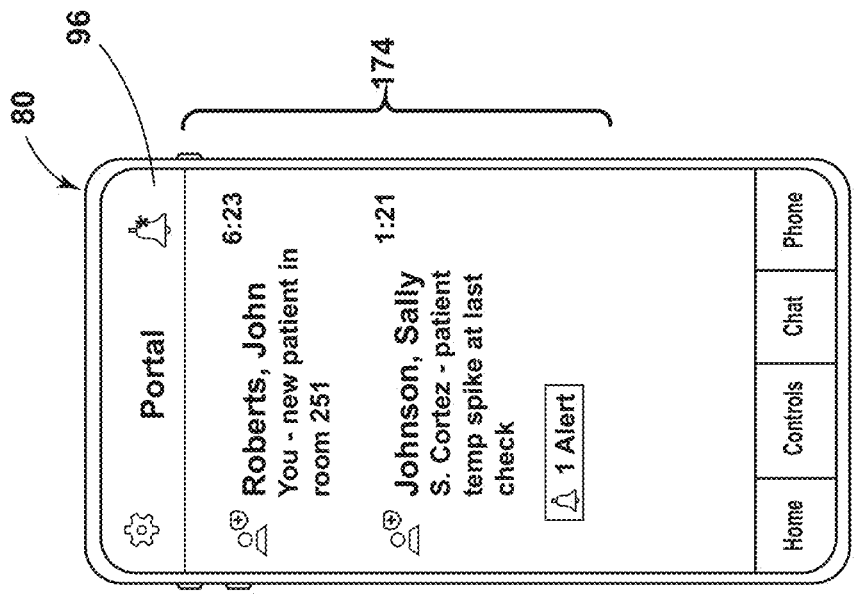
FIG. 6 is representative of a patient portal of a caregiver interaction system displayed on a remote device associated with an information system, according to the present disclosure.
Figure 5:
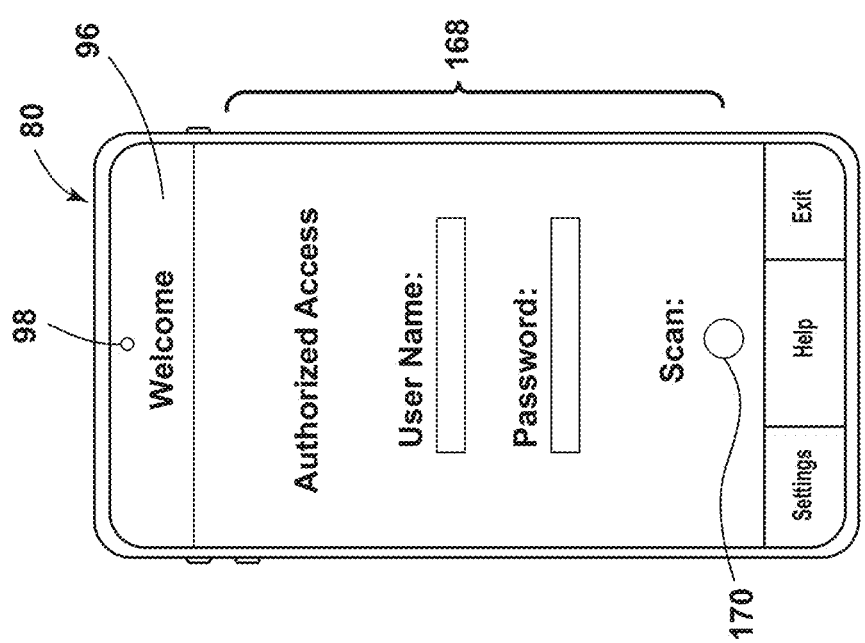
FIG. 5 is representative of an authorized access interface of a remote device associated with an information system, according to the present disclosure.
Figure 7:
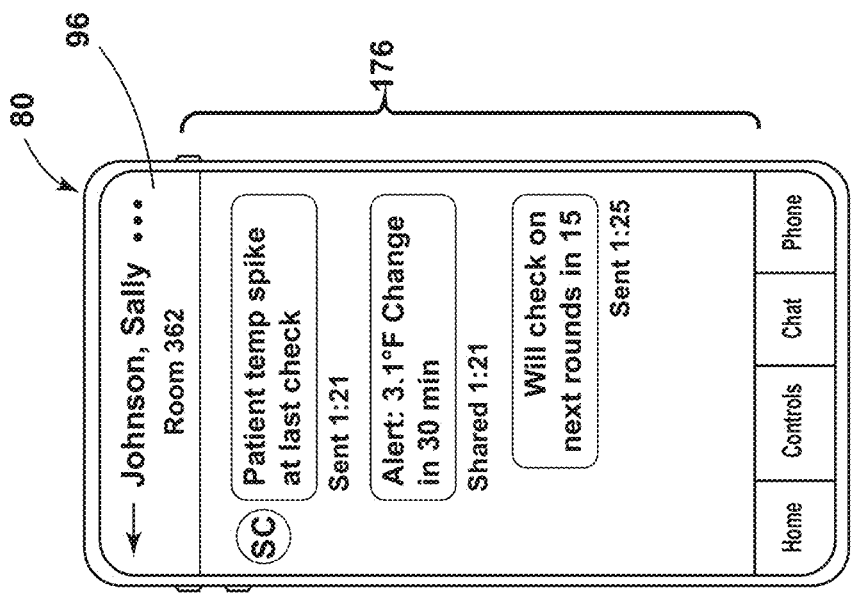
FIG. 7 is representative of a chat feature of a caregiver interaction system displayed on a remote device associated with an information system, according to the present disclosure.

Referring again to FIG. 2, as well as FIGS. 5-7, the controller 18 may be associated with the caregiver interaction system 122 accessible via an application interface on, for example, the remote device 20, a facility device (such as at a nurse call station), or other devices. The caregiver interaction system 122 may be accessible via an application or software on the remote device 20. The caregiver interaction system 122 provides communication between some or all of the caregivers associated with the patient during the treatment or stay of the patient at the medical facility 12. The caregiver interaction system 122 may also provide a process for communicating information about the patient between caregivers, as well as to the electronic medical record 120 (FIG. 2).

In the illustrated example of FIGS. 5-7, the handheld device 80 is illustrated with information conveyed to the caregiver via the display 96. As illustrated in FIG. 5, an authorized access interface 168 is provided on the handheld device 80 to receive the credentials or other identification information of the caregiver. The caregiver may input access information (e.g., user name and password) to gain access to the caregiver interaction system 122 and additional facility systems, such as the information system 10.

Additionally or alternatively, the handheld device 80 may have a touch identification feature 170 for recognizing a fingerprint (e.g., identification information) of the caregiver. The touch identification feature 170 includes a sensor or imager for sensing the fingerprint of the caregiver. The sensed fingerprint may be compared to a stored image within the memory 86 of the handheld device 80 to confirm access to the caregiver interaction system 122 and the information system 10. The information system 10 may also store images of caregiver fingerprints and the handheld device 80 may communicate with the information system 10 to confirm access of the caregiver. At least one of the controller 18 of the information system 10 and the handheld device 80 includes routines 58, 88 for comparing the sensed fingerprint with stored data to confirm authorization and access of the caregiver.

In additional examples, the handheld device 80 may include the additional imager 98, which may be utilized to obtain identification information, such as facial recognition or eye recognition (e.g., iris authentication), to grant access to the caregiver. The additional imager 98 may be a rearward facing imager on the same side of the handheld device 80 as the display 96. The imager 98 may be configured to capture image data of the face of the caregiver for identification and authorization purposes. The captured image data of the face of the caregiver may be compared to stored images in the handheld device 80 or in the controller 18 of the information system 10. At least one of the controller 18 of the information system 10 and the handheld device 80 includes routines 58, 88 for comparing the detected image of the caregiver with the stored data to determine access of the caregiver.

As best illustrated in FIG. 6, the caregiver is able to access the caregiver interaction system 122 via the authorized access interface 168, the touch identification feature 170, the facial recognition, or eye recognition. Once access is granted to the caregiver interaction system 122, the caregiver has access to a portal 174 that displays a variety of information about the patient or patients associated with the caregiver. The portal 174 may display messages from other caregivers, alerts, patient information 48, facility protocols 126, and other information helpful for providing care for the patient. The portal 174 may provide updates to the caregiver about the patient organized in a single location.

The information and systems accessible by the caregiver may depend on the level of access of the caregiver or the role of the caregiver. For example, the information system 10, may enable features depending on the role of the individual or user to provide role based access controls (RBAC) for the individual that is signed into the information system 10. In such examples, a nurse may view certain patient details or have different options that a technician might not see.

As best illustrated in FIG. 7, the caregiver interaction system 122 provides a chat feature 176 for caregivers to communicate with one another about the patient (e.g., share the patient information 48) and the treatment for the patient. The information shared in the chat feature 176 may not be information that is stored in the electronic medical record 120 (FIG. 2). Accordingly, the caregiver interaction system 122 is another system within the medical facility 12 that includes the patient information 48 and/or the device information 26 that may be retrieved by the controller 18 and conveyed to the caregiver as part of the information system 10. Moreover, the virtual image 30 generated by the controller 18 of the information system 10 may be communicated to other caregivers associated with the patient via the chat feature 176.

It is contemplated that the caregiver interaction system 122 may also be viewed or accessed via the wearable device 100. In such configurations, the controller 18 may generate and project the virtual image 30 having the authorized access interface 168. The sensors 112, 114 may sense identification information based on the movement or gestures of the caregiver. The sensors 112, 114 may also sense or scan an identification badge, which provides the identification information utilized for accessing the various systems. Additionally or alternatively, the user sensors 114 may be configured for facial recognition and/or iris authentication to grant access to the information system 10.

Figure 9:
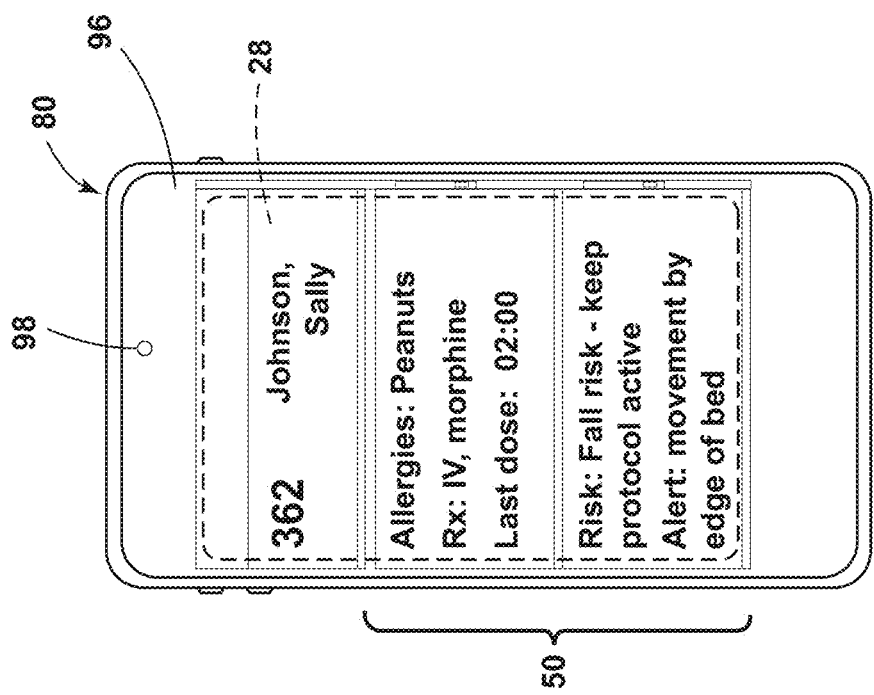
FIG. 9 is representative of an image overlaid on captured image data and displayed on a remote device, according to the present disclosure.
Figure 10:
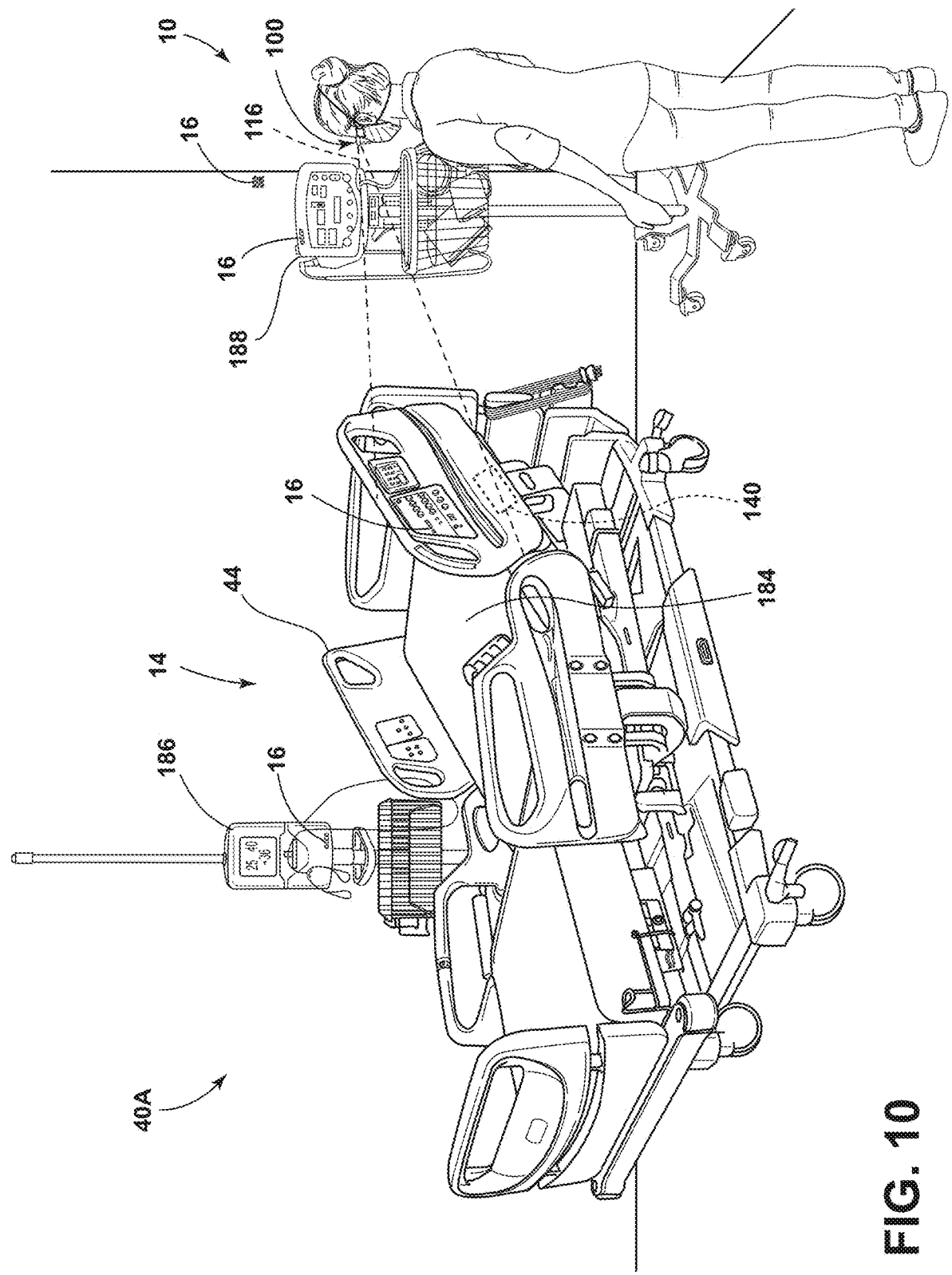
FIG. 10 is a schematic view of a caregiver in a room environment and using a wearable remote device, according to the present disclosure.

Referring again to FIG. 2, as well as FIGS. 8 and 9, the information system 10 is illustrated using augmented reality to display information through the display 96 of the handheld device 80. The caregiver arranges the handheld device 80 to position the imager 92 relative to the visual identifier 16. The imager 92 captures image data (e.g., real-world data) in the field of detection 24 and communicates the captured image data to the control unit 82. The image data includes the visual identifier 16, which is illustrated on a room plaque 180 (e.g., the query member 36) outside the patient room 40A in the example in FIG. 8. The visual identifier 16 may be a barcode, a quick response (QR) code, a pattern, an image, etc. identifiable and distinguishable by the information system 10.

The image data relating to the visual identifier 16 is communicated from the handheld device 80 to the controller 18 of the information system 10. The controller 18 includes at least one routine 58 for analyzing the visual identifier 16 and determining the information associated with the visual identifier 16 to be retrieved. The controller 18 may process the image data to determine the specific configuration of the visual identifier 16, which allows the controller 18 to determine at least one of the query member 36 with which the visual identifier 16 is associated and the information to be retrieved. Further, the controller 18 retrieves the information from at least one information source 28, including at least one of the electronic medical record 120, the facility protocols 126, the treatment device 14, the local server 50, the remote server 52, and the caregiver interaction system 122 via the wired or wireless protocols disclosed herein.

The controller 18 retrieves and compiles the data or information associated with the visual identifier 16 and generates the virtual image 30, which includes some or all of the retrieved information. Some information may be restricted based on the access level of the caregiver. For example, the information system 10 may be the RBAC system, which provides different information to different roles at the medical facility 12. Certain caregivers may utilize more or different information to treat or care for the patient. The information presented to the caregiver in the virtual image 30 may be roles-based, allowing for select information to be presented to the caregiver based on the specific role or position of the caregiver. The virtual image 30 may include text, graphics, images, charts, graphs, etc. that convey information to the caregiver. The image data may be communicated to the controller 18 and the controller 18 overlays the virtual image 30 on the image data and communicates the combined image data to the handheld device 80 to be viewed on the display 96. Alternatively, the virtual image 30 may be communicated to the handheld device 80 and the handheld device 80 may combine the virtual image 30 with the image data.

For example, in the illustrated configuration of FIGS. 8 and 9, the caregiver positions the handheld device 80 to capture the visual identifier 16 on the room plaque 180 within the field of detection 24. The imager 92 captures the image data, including the visual identifier 16, the room plaque 180, and a room number 182 within the field of detection 24. The controller 18 analyzes the visual identifier 16 within the image data and associates the visual identifier 16 with the patient information 48, the device information 26, or a combination thereof based on the specific visual identifier 16. The controller 18 retrieves the patient information 48 and the device information 26 and generates the corresponding virtual image 30.

Referring still to FIGS. 8 and 9, the virtual image 30, overlaid on the captured image data of the room plaque 180, is displayed via the display 96 of the handheld device 80, as best illustrated in FIG. 9. Accordingly, the virtual image 30 augments the real-world view of the room plaque 180 by displaying the virtual patient information 48 over the real-world image data. The patient information 48 includes information that may be relevant or important for the caregiver prior to entering the patient room 40A. The patient information 48 may include, for example, a patient name, allergies, current or historical medications, medication dose information, risk information, alerts associated with the patient, as well as any other information that may be useful for the caregiver. The illustrated patient information 48 is exemplary and not meant to be limiting. The virtual image 30 may replace or supplement a traditional patient chart. Further, the location of the visual identifier 16 on the room plaque 180 is also exemplary.

It is contemplated that each room environment 40 within the medical facility 12 includes the room plaque 180, which may include the respective visual identifier 16. Additionally or alternatively, a surface, such as on a wall, within the room environment 40 may include the visual identifier 16. The visual identifier 16 associated with the room environment 40 may be utilized for conveying information about the room environment 40 (e.g., lighting conditions, temperature, etc.), procedures, treatments, the patient, schedule, or a combination thereof. Accordingly, the room environment 40 may also be an example of the query member 36 in which the caregiver seeks information. Further, it is also contemplated that the alerts or alarms presented in the virtual Image 30 may be associated with the nurse call system 124. The nurse call system 124 indicates to the caregiver that the patient is in need of assistance.

The visual identifier 16 may be changed or adjusted for each patient. In such examples, the visual identifier 16 may be replaced when the patient is no longer in the specific room environment 40. Alternatively, the information associated with the visual identifier 16 may be changed or adjusted by changing the routines 58 of the information system 10. In such examples, the visual identifier 16 remains at the select room environment 40, but the controller is re-programmed (e.g., via new or adjusted routines 58) to associate new or changed information with the visual identifier 16.

Referring again to FIG. 2, as well as FIGS. 10-13, the patient room 40A is illustrated with a variety of treatment devices 14 including the medical bed 44, a mattress 184, an oxygen therapy device 186, and a vital signs monitor 188, which may each be an exemplary configuration of the query member 36. The illustrated treatment devices 14 are exemplary and not meant to be limiting. Other treatment devices 14, such as a microclimate management system associated with the mattress 184, a pneumatic system associated with the mattress 184, sequential compression devices, sub-epidermal moisture (SEM) scanners, and/or the surgical table 46 may be included in the patient room 40A, the surgical suite 40B, or elsewhere in the medical facility 12 without departing from the teachings herein.

Each treatment device 14 includes the visual identifier 16, which is associated with the specific treatment device 14. The visual identifiers 16 in each location (e.g., each treatment device 14, each room plaque 180 within the medical facility 12, etc.) are different to allow the controller 18 to associate specific information with each visual identifier 16. The controller 18 is configured to analyze the location information based on the configuration of the visual identifier 16 to determine the information associated with each specific visual identifier 16.

It is contemplated that other objects within the room environment 40 may also include data tags 16 or visual identifiers 16. For example, when at the medical facility 12, the patient generally wears the patient identification feature 38 (e.g., an identification bracelet 38). The identification bracelet 38 may include the visual identifier 16. In another example, a wall within the room environment 40 may have a visual identifier 16 that conveys information about the room environment 40, such as temperature or lighting information. Each of these objects that includes the specific visual identifier 16 is an exemplary configuration of the query member 36, which the caregiver is seeking information about via the information system 10.

The caregiver may use the handheld device 80 to view the information associated with the visual identifiers 16, as previously discussed herein, and/or may use the wearable device 100 to view the information using augmented reality or mixed reality. When using the wearable device 100 for mixed reality, the caregiver uses the environmental sensors 112 to obtain image data or other data relating to the surrounding environment. The environmental sensors 112 sense or the visual identifier 16 within the field of view 116 and communicate the data relating to the visual identifier to the control unit 102. The data may be communicated as image data or other data depending on the type of sensor.

The control unit 102 communicates the information relating to the visual identifier 16 to the controller 18 of the information system 10, which analyzes the visual identifier 16 and retrieves the associated information (e.g., the device information 26, the patient information 48, etc.). The controller 18 generates the virtual image 30 with the associated information and communicates the virtual image 30 to the wearable device 100. The virtual image 30 is then projected via the projector 118 into the field of view 116 of the caregiver. In this way, the caregiver may view his or her surrounding environment with the virtual image 30 incorporated into the surrounding environment.

The device information 26 may include information from the treatment device 14 that relates to the operation of the treatment device 14 and/or information about the patient using the treatment device 14. In the example illustrated in FIG. 11, the treatment device 14 is configured as the medical bed 44. The medical bed 44 includes the sensor assembly 140, which may include sensors that sense information about the status of the medical bed 44 and sensors that sense information about the status of the patient. The information sensed by the sensor assembly 140 is generally conveyed to the caregiver via the information system 10 in the virtual image 30. The device information 26 for the medical bed 44 may include, for example, a type of medical bed 44, functions of the medical bed 44, safety states in accordance with the facility protocols 126, ongoing alerts, active therapies, current positions, activated protocols, etc.

In various aspects, the sensor assembly 140 may sense a variety of information about the status of the medical bed 44. For example, the sensor assembly 140 may sense whether a braking system of the medical bed 44 is properly initiated. In another example, the medical bed 44 includes an obstacle detection system, and the sensor assembly 140 senses objects within a movement path of a lift system that raises and lowers a support surface of the medical bed 44. Additionally or alternatively, the medical bed 44 generally articulates between different positions (e.g., head elevated, foot elevated, etc.) and the sensor assembly 140 may sense the position of the medical bed 44. In an additional example, the medical bed 44 or components coupled to the medical bed 44 may be powered by a battery. The sensor assembly 140 may sense additional components coupled with the medical bed 44, as well as a charge level of the medical bed 44 or the associated components.

The sensor assembly 140 may also sense information about the patient on the medical bed 44. For example, the medical bed 44 may include a monitoring system, which monitors a position and/or movement of the patient on the support surface. The monitoring system may include pressure sensors (e.g., of the sensor assembly 140) that monitor the weight distribution of the patient related to predetermined movement thresholds and/or relative to a predetermined center of gravity. The control unit 130 may compare subsequent information from the pressure sensors to determine the movement of the patient. Additionally, the patient information 48 from the medical bed 44 may include health metrics of the patient, such as heart rate or respiration rate, sensed via generally contact-free patient monitoring.

The information from the treatment device 14, including information from the sensor assembly 140, may be included in the virtual image 30 generated by the controller 18. Further, this information may be compared to the facility protocols 126. In such configurations, the controller 18 retrieves or processes the facility protocols 126 from the remote server 52 and compares the information from the treatment device 14 and the patient information 48 with the facility protocols 126. The controller 18 may then generate the virtual image 30 with information about the facility protocols 126, such as an alert that the facility protocols 126 are not currently being followed and a prompt to adjust the treatment device 14 to follow the facility protocol 126.

Figure 11:
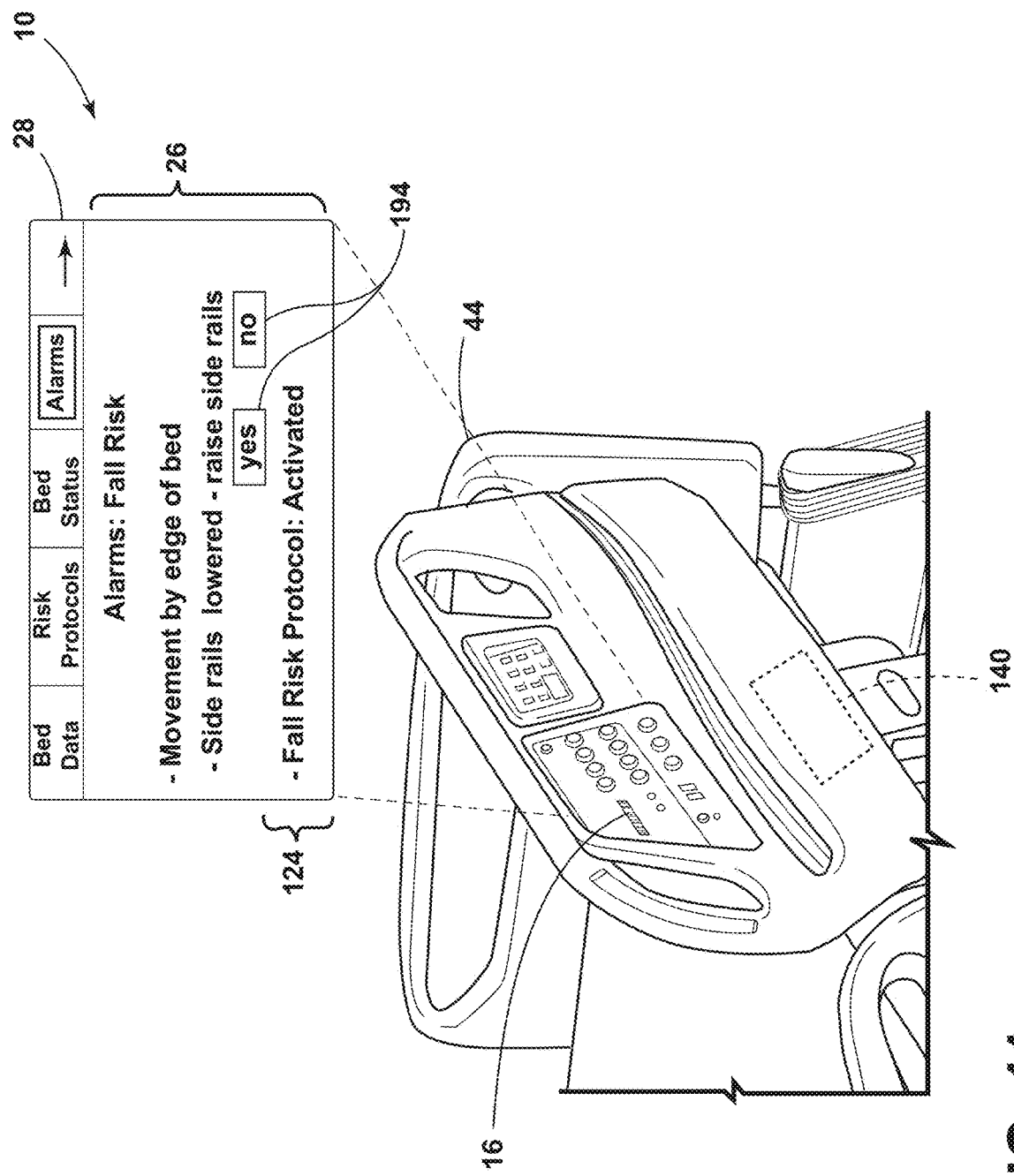
FIG. 11 is a schematic view of a virtual image including information associated with a medical bed projected for a caregiver to view with a wearable remote device, according to the present disclosure.

Referring still to FIGS. 2 and 10-12, there are multiple facility protocols 126 that may be utilized by the information system 10. For example, the facility protocols 126 may include a fall risk protocol. When the fall risk protocol is initiated, the patient may not exit the medical bed 44 or other support apparatus or surface without the assistance of the caregiver due to a heightened risk that the patient may fall or be injured. The monitoring system of the medical bed 44 monitors the movement of the patient and if the patient is sensed proximate to an edge of the medical bed 44, the virtual image 30 may include an alert or alarm to notify the caregiver of the risk to the patient, as illustrated in FIG. 11.

Additionally or alternatively, if the monitoring systems senses movement of the patient and a siderail of the medical bed 44 is lowered (as sensed by the sensor assembly 140), the virtual image 30 may include an alert that the patient may be trying to exit the medical bed 44. When using mixed reality, the virtual image 30 may include selectable features 194. The caregiver may interact with the selectable features 194 within the virtual image 30. The selectable features 194 may activate certain protocols or adjust certain aspects of the medical bed 44. For example, as illustrated in FIG. 11, the caregiver may select whether to raise the side rails of the medical bed 44. The selection or interaction with the virtual image 30 may be sensed by at least one of the environmental sensors 112 and the user sensors 114 and compared to the virtual image 30. The wearable device 100 may then communicate the command or selection of the user to the medical bed 44.

As illustrated in FIG. 11, the virtual image 30 is showing information related to alarms. The virtual image 30 may be adjusted or changed in response to the movement of the caregiver. For example, the caregiver may swipe his hand in a left-to-right gesture, which may adjust the virtual image 30 to the "Bed Status" information. Additionally or alternatively, the headings or titles in the virtual image 30 (e.g., "Bed Date," "Risk Protocols," "Bed Status," "Alarms," etc.) may be selectable features 194. The caregiver may point to the heading to change the virtual image 30 to include or display new or additional information. The environmental sensors 112, the user sensors 114, or both may track the movement and/or focus of the caregiver to sense the gesture or selection of the caregiver. The movement and/or the focus of the caregiver may be analyzed by the control unit 102 and/or the controller 18 and compared to the virtual image 30 to determine the selection or the input from the caregiver.

In another example, the facility protocols 126 may include a pulmonary risk protocol. When the pulmonary risk protocol is activated, the sensor assembly 140 may monitor the head position of the patient. Generally, the head position is elevated at least about 30° relative to a flat position. If the head of the patient is not elevated, the virtual image 30 may include an alert that the head of the patient should be elevated and may also include a prompt to adjust the medical bed 44 to elevate the head of the patient, which may be selected via the virtual image 30. An adjustment assembly of the medical bed 44 may be activated in response to the selection in the virtual image 30 to adjust the elevation angle of the head end of the medical bed 44.

Referring again to FIGS. 2, 12, and 13, the treatment device 14 may be the vital signs monitor 188, which generally communicates the patient information 48 to the information system 10. It is contemplated that the vital signs monitor 188 may also communicate device information 26, such as a status of the vital signs monitor 188, alerts regarding the function of the vital signs monitor 188, etc. The vital signs monitor 188 may include the sensor assembly 140 having a variety of physiological sensors to obtain vital signs information from the patient, including, but not limited to, core body temperature or skin temperature, pulse rate, heart rate, blood pressure, respiratory rate, body weight, other body signs such as end-tidal $CO_2$, $SpO_2$ (saturation of oxygen in arterial blood flow), and other indicators of the physiological state of the patient. The caregiver may utilize the wearable device 100 to view the information associated with the visual identifier 16 coupled to the vital signs monitor 188.

Figure 12:
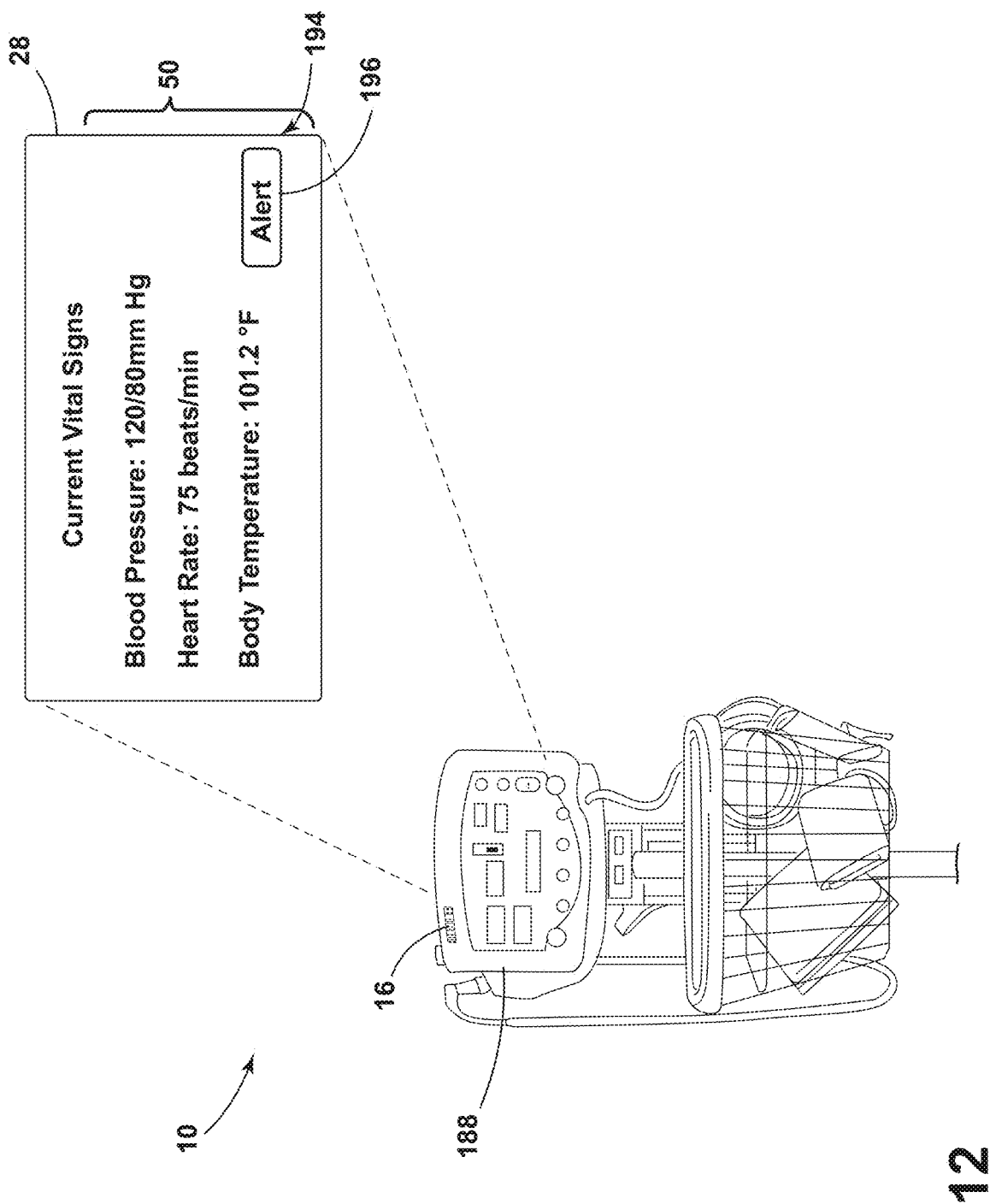
FIG. 12 is a schematic view of a virtual image including patient information projected for a caregiver to view with a wearable remote device, according to the present disclosure.
Figure 13:
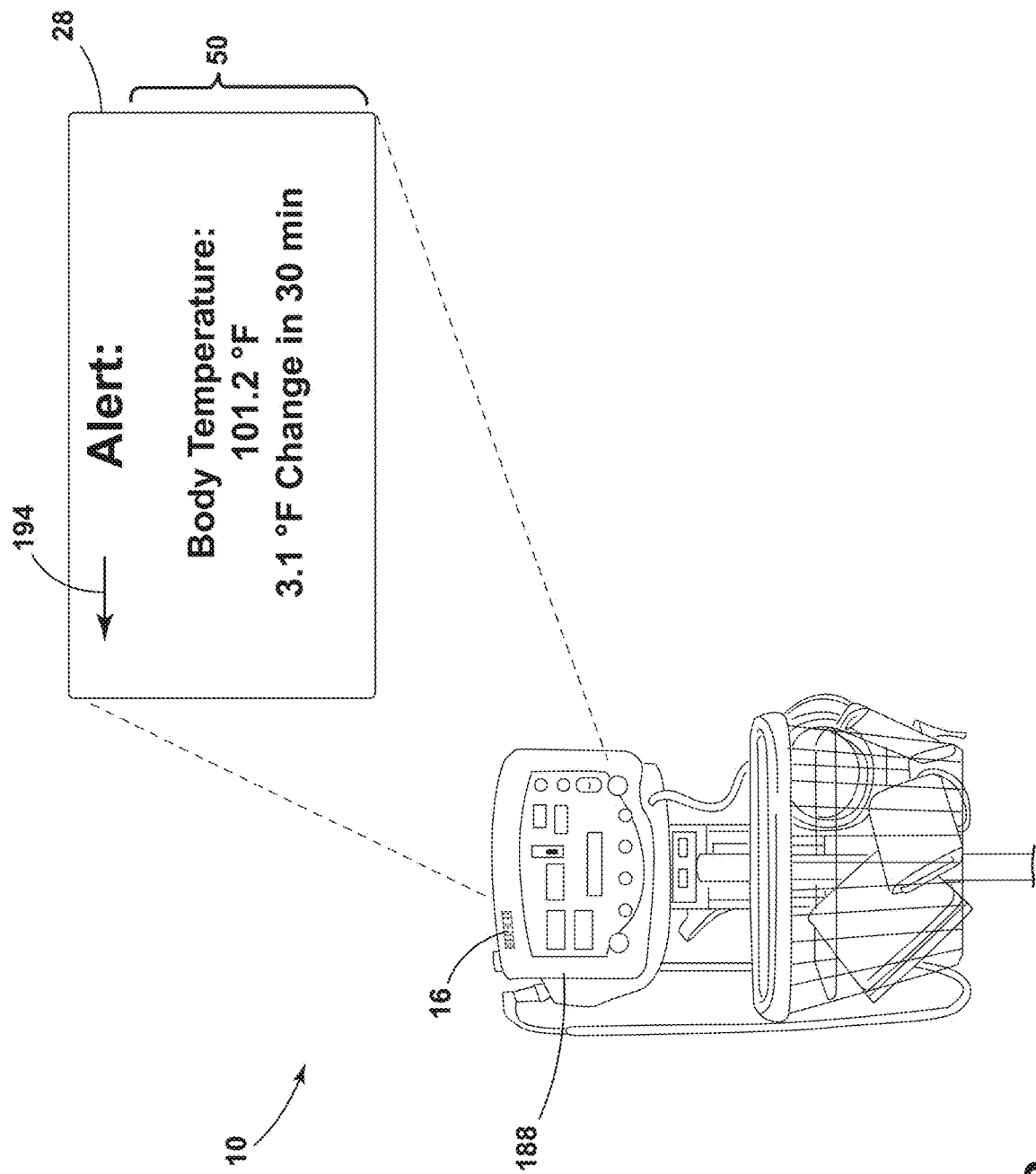
FIG. 13 is a schematic view of an updated image projected after interaction with the image of FIG. 12.

As illustrated in FIG. 12, the virtual image 30 includes the patient information 48 relating to blood pressure, heart rate, and body temperature. The illustrated virtual image 30 includes an alert feature 196 proximate the body temperature information. The caregiver may interact with the virtual image 30 to select the alert feature 196 (e.g., an exemplary selectable feature 194), which changes the virtual image 30 to display the alert information illustrated in FIG. 13.

When using the wearable device 100, the caregiver may interact with and manipulate the virtual image 30. The environmental sensors 112 and/or the user sensors 114 may sense the movement or gestures of the caregiver. The control unit 102 of the wearable device 100 may compare the movement of the caregiver with the virtual image 30 projected from the projector 118. The control unit 102 may identify the selection of the caregiver and communicate the selection to the controller 18 so the controller 18 may generate the subsequent or updated virtual image 30 in response to the selection. The updated virtual image 30 may then be communicated to the control unit 102 and projected into the field of view 116 of the caregiver.

Referring again to FIGS. 10-13, as the caregiver moves about the patient room 40A, or any other room environment 40, the caregiver may see multiple virtual images 30 depending on the field of view 116. The wearable device 100 monitors the head and eye position of the caregiver to track the focus of the caregiver. The virtual images 30 projected into the field of view 116 of the caregiver may be adjusted relative to the caregiver as a real-world object would. For example, as the caregiver moves closer to the virtual image 30, the virtual image 30 appears larger as if the caregiver is approaching a real object. The caregiver may move, adjust, and otherwise manipulate the virtual image 30 when using the wearable device 100. It is contemplated that each visual identifier 16 within the patient room 40A may also be sensed with the handheld device 80, which would allow the caregiver to view the device information 26 and the patient information 48 via the display 96 using augmented reality.

Referring to FIGS. 1-13, the caregiver may use augmented reality, mixed reality, or both to view a variety of information relating to the patient, the treatment device 14, the room environment 40, etc. Visual identifiers 16 or other data tags 16 may be disposed in a variety of locations throughout the medical facility 12 on a variety of query members 36. Each visual identifier 16 is unique and is associated with specific information, allowing the information system 10 to retrieve the information associated with certain visual identifiers 16 for the caregiver. The visual identifiers 16 associated with the patient may be updated via the information system 10 when the patient is discharged or may be replaced. The remote device 20 is in communication with the information system 10 to display the virtual image 30 generated by the controller 18 to the caregiver. The information system 10 provides an efficient and convenient process for the caregiver to view information that is generally stored in multiple locations.

In augmented reality examples, the virtual image 30 that includes the added information (e.g., the device information 26, the patient information 48, etc.) is a generated image overlaid on captured or sensed image data and displayed together to the caregiver on the display 96. The virtual image 30 augments the real-world image obtained by the remote device 20. In mixed reality examples, the virtual image 30 is a generated image projected from the remote device 20 into the field of view 116 of the caregiver. The virtual image 30 is incorporated into the real-world surroundings of the caregiver, and the caregiver may manipulate or interact with the virtual image 30. The caregiver, who has been granted access to the information system 10, may view the information in the virtual image 30, but others around the caregiver or others in the medical facility 12 may not view the information without obtaining access through the remote device 20. In this way, the information system 10 maintains heightened privacy of the information in the virtual image 30.

Additionally or alternatively, different caregivers may have different levels of access. When the caregiver is identified by the information system 10, different information may be included in the virtual image 30 to include the information for which the caregiver has access. Additional authorized information may not be included in the virtual image 30. It is contemplated that a notification may be presented to the caregiver that access is unauthorized or limited.

Figure 14:
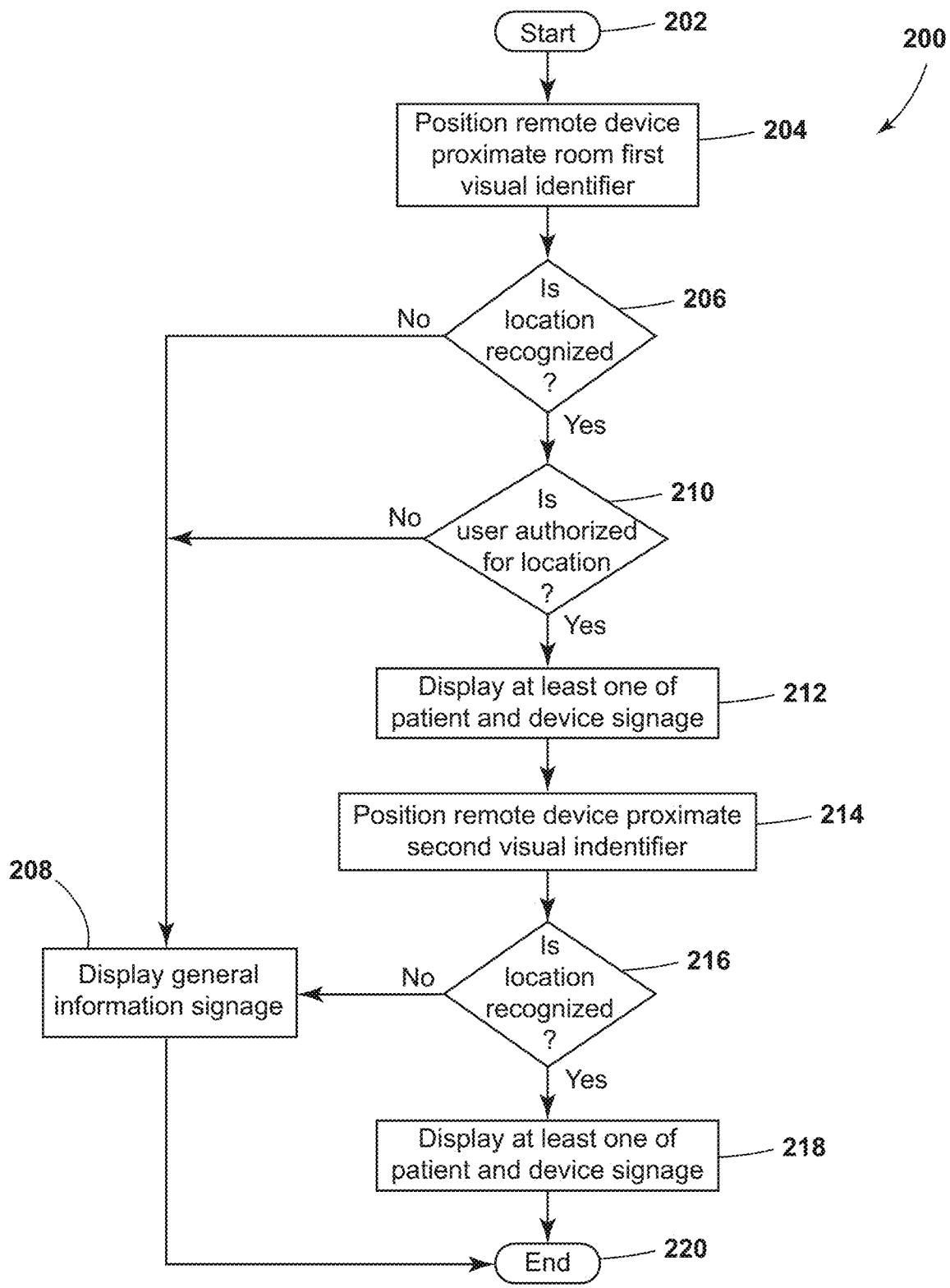
FIG. 14 is a flow diagram of a method for displaying information to a caregiver, according to the present disclosure.

Referring to FIG. 14, as well as FIGS. 1-13, a method 200 of displaying information to the caregiver starts at 202 with activation of the remote device 20 and proceeds to step 204 where the remote device 20 is positioned proximate to the room plaque 180 or other location outside of a room environment 40. The remote device 20 is oriented to sense the first or initial visual identifier 16. The visual identifier 16 may be any symbol, barcode, QR code, text, graphic, characters, codes, or data that may be optically recognized. In examples using the handheld device 80, the handheld device 80 is positioned such that the field of detection 24 of the imager 92 includes the visual identifier 16. In wearable device 100 examples, the caregiver positions his or her head such that the visual identifier 16 is within the field of detection 24 of the environmental sensors 112, which may generally align with the field of view 116 of the caregiver. Generally, if the caregiver is positioned directly in front of the room plaque 180, the environmental sensors 112 can sense the visual identifier 16.

Further, in step 204, the remote device 20 may sense the surrounding environment and/or capture image data. Additionally, in step 204, the remote device 20 senses the visual identifier 16 and communicates the information relating to the visual identifier 16 to the controller 18. The remote device 20 may also communicate image data relating to the surrounding environment to the controller 18.

In decision step 206, the controller 18 receives and analyzes the information related to the visual identifier 16 from the remote device 20. Each visual identifier 16 is unique. For example, each visual identifier 16 is associated with a location, which corresponds with a specific treatment device 14, room environment 40, and/or patient. The location may be the identifying or unique information (e.g., the configuration) in the visual identifier 16 that allows the information system 10 to recognize and correlate the specific information to be retrieved with the visual identifier 16. In a non-limiting example, the visual identifier 16 on the room plaque 180 is associated with the specific patient room 40A, the patient in the patient room 40A, or both. In another non-limiting example, the visual identifier 16 on a patient identification bracelet (e.g., the identification feature 38) is associated with the specific patient. In decision step 206, the controller 18 determines whether the location of the visual identifier 16 is recognized.

If the location of visual identifier 16 is not recognized in decision step 206, the information system 10 proceeds to step 208. In step 208, the controller 18 generates the virtual image 30, which includes more general, non-confidential information. This more general information may include device information 26, such as a manufacturer, charge level, location of the treatment device 14 within the medical facility 12 (e.g., floor 42, unit, etc.), as well as more general information about the medical facility 12, such as facility name, location of nurse call stations, and location of exits. Without recognition of the location, the information system 10 may not associate the specific information about the treatment device 14 or the patient with the visual identifier 16.

Returning to decision step 206, if the controller 18 recognizes the location, the information system 10 proceeds to decision step 210 to determine whether the caregiver with the remote device 20 has authorized access to the information associated with the location of the visual identifier 16. The controller 18 communicates with remote device 20, which includes the authorized access interface 168. If the caregiver has been granted access via the authorized access interface 168, touch identification feature 170, facial recognition, or iris authentication, the controller 18 recognizes the authorization of the caregiver to access some of all of the information.

There may be different levels of access for different caregivers, which may be based on the individual caregiver, the role of the caregiver, the seniority of the caregiver, etc. The level of access granted to each caregiver or each type of caregiver (e.g., nurse, technician etc.) may be stored within the memory 56 of the information system 10. The level of access may be associated with the stored identification information (e.g., credentials, fingerprint information, stored facial or iris image, etc.). The controller 18 may then grant access to the authorized information or options, and may not include any unauthorized information or options within the virtual image 30. Accordingly, the virtual image 30 may be different for caregivers having different authorization levels. If the user is not authorized for any of the information associated with the specific visual identifier 16, the information system 10 proceeds to step 208 to display the more general information.

Returning to decision step 210, if the caregiver is authorized to view or access at least some of the information associated with the visual identifier 16, the information system 10 proceeds to step 212 of generating the virtual image 30 to include at least one of the patient information 48, the device information 26 for treatment devices 14 in the room environment 40, and information associated with the room environment 40 (e.g., room information). The virtual image 30 is generated and communicated to the remote device 20. The patient information 48 and/or room information associated with the room plaque 180 is then displayed to the caregiver. The virtual image 30 with the patient information 48 and/or the room information may be overlaid on the captured image data and displayed via the handheld device 80, may be projected into the field of view 116 of the caregiver using the wearable device 100, or a combination thereof. Accordingly, the virtual signage having confidential information may be displayed to the caregiver, thereby being viewable by the caregiver and not others in the surrounding area. The confidential information may include information helpful for the caregiver to know prior to entry into the room environment 40.

In step 214, the caregiver may enter the room environment 40, such as the patient room 40A, associated with the room plaque 180. The caregiver may position the remote device 20 to sense at least one subsequent visual identifier 16 within the room environment 40. The visual identifier 16 may be associated with the patient, with at least one treatment device 14, the room environment 40 in general, or other objects or systems within the room environment 40.

In decision step 216, the controller 18 receives the information relating to the subsequent visual identifier 16 and determines whether the location of the visual identifier 16 is recognized, similar to decision step 206. If the location is not recognized, the information system 10 proceeds to step 208 of displaying the virtual signage with more general information. Without the location being recognized, the controller 18 may not be able to determine the information associated with the visual identifier 16 to be retrieved.

If in decision step 216 the location of the visual identifier 16 is recognized, the information system 10 proceeds to step 218 of generating the virtual image 30 and displaying the virtual image 30 (e.g., the virtual signage) to the caregiver. The controller 18 may utilize the access level of the caregiver determined in decision step 210 and display the information according to the access level of the caregiver. Alternatively, the controller 18 may confirm the access level of the caregiver in step 218. The access level may differ for each visual identifier 16.

Additionally, in step 218, the caregiver may view or interact with the virtual image 30 to obtain the desired information about the patient, the treatment device 14, the room environment 40, etc. The virtual image 30 may also include facility protocols 126 and prompts to activate facility protocols 126 based on the information from the treatment device 14, the electronic medical records 120, or the caregiver interaction system 122. Additionally, the virtual image 30 may provide a prompt for action based on or aligned with the facility protocols 126.

Further, in step 218, the controller 18 may generate additional virtual images 30 in response to recognizing other visual identifiers 16 within the surrounding environment. Additionally or alternatively, the controller 18 may generate subsequent or updated virtual images 30 based on the interaction of the caregiver with the virtual image 30, new information available and retrieved by the controller 18, the position of the caregiver relative to the virtual image 30, or a combination thereof. The updated virtual image 30 may replace a previous virtual image 30 or supplement the previous virtual image 30 to include additional information. The virtual image 30 may be automatically updated in response to sensed information, at predefined intervals, etc.

In step 220, the virtual image 30 may be stored within the memory 56 of the controller 18, the remote device 20, the electronic medical record 120 of the patient, or a combination thereof. Additionally, the virtual image 30 may be shared or communicated to other caregivers via the caregiver interaction system 122. When the virtual image 30 has been viewed by the caregiver, the caregiver may terminate the display of the virtual image 30, and the method 200 ends at 222. It is understood that the steps 202-222 of the method 200 may be performed in any order, simultaneously, repeated, and/or omitted without departing from the teachings provided herein.

With reference to FIGS. 1-13, the information system 10 provides an efficient process for the caregiver to view information from a variety of sources 28 simultaneously, while the confidentiality of the information is maintained. The caregiver views the device information 26, the patient information 48, and/or the room information in the virtual image 30 via augmented reality or mixed reality. The information system 10 provides selective access to the information, which heightens patient privacy. The virtual image 30 is generated in response to specific visual identifiers 16 or other data tags identified by the information system 10. The information system 10 compiles information from the treatment devices 14, the electronic medical record 120, the caregiver interaction system 122, the local server 50, the remote server 52, the facility protocols 126, the sensor assembly 140, and any other system or device associated with the medical facility 12. In this way, the virtual image 30 provides a single location for the caregiver to view information that is useful for treating and caring for the patient. The information system 10 also provides multiple virtual images 30 to provide the information to the caregiver in updated, supplemented, or new virtual images 30.

The data tag configured as the visual identifier 16 may be any optically recognizable feature identifiable by the information system 10. It is contemplated that other configurations of the data tag using additional or alternative modes of sensing information, such as radio frequency identification (RFID) tags, location tags, etc., may be utilized by the information system 10 to determine the information to be provided to the caregiver without departing from the teachings herein. The information system 10 may include one or several modes of sensing information.

Use of the present system may provide for a variety of advantages. For example, the caregiver may retrieve information from a variety of locations or sources 28 using the information system 10, which increases the efficiency of the caregiver in treating the patient. Additionally, the caregiver may view the information in at least one virtual image 30 generated by the information system 10 and displayed directly to the caregiver. Further, the caregiver may provide increased contactless care by utilizing the information system 10, rather than using hard copies of handwritten notes and other hardware. Also, the information system 10 may utilize augmented reality to overlay the virtual image 30 on image data to be displayed by the handheld device 80. Additionally, information system 10 may use mixed reality to project the virtual image 30 into the field of view 116 of the caregiver wearing the wearable device 100. Further, when utilizing the wearable device 100, the caregiver may interact with or manipulate the virtual image 30. Moreover, the information system 10 may provide greater privacy to the patient. The information system 10 may also reduce human-based errors, by populating information into the virtual image 30 automatically. Additionally, the information system 10 may increase convenience and accessibility to data regardless of where the data is stored. Additional benefits or advantages of using this system may be realized and/or achieved.

The memories disclosed herein may be implemented in a variety of volatile and nonvolatile memory formats. The controller and control units described herein may include various types of control circuitry, digital or analog, and may include a processor, a microcontroller, an application specific integrated circuit (ASIC), or other circuitry configured to perform various inputs or outputs, control, analysis, and other functions described herein.

The device and method disclosed herein is further summarized in the following paragraphs and is further characterized by combinations of any and all of the various aspects described therein.

According to at least one aspect of the present disclosure, an information system for displaying virtual signage in a medical facility includes a treatment device. A visual identifier is operably coupled to the treatment device and a controller is configured to communicate with a remote device having a sensor for sensing the visual identifier within a field of detection. The controller is configured to recognize the visual identifier sensed by the remote device, determine device information associated with the visual identifier based on a configuration of the visual identifier, retrieve the device information relating to the treatment device associated with the visual identifier from an information source, and generate a virtual image including the device information configured to be viewed via the remote device.

According to another aspect, a treatment device is at least one of a mattress, a medical bed, a surgical table, and a vital signs monitor.

According to another aspect, a controller is configured to retrieve patient information from an electronic medical record stored in a server. A virtual image includes the patient information from the electronic medical record.

According to another aspect, a controller is configured to overlay a virtual image on image data sensed by a remote device. The controller is configured to communicate the virtual image combined with the image data to the remote device to be displayed.

According to another aspect, a controller is configured to communicate a virtual image to a remote device to be projected into a field of view of a user wearing the remote device.

According to another aspect, a controller is configured to communicate with a sensor of a remote device that is configured to sense at least one of movement of a user of the remote device and a focus direction of the user. The controller is configured to generate an updated virtual image in response to at least one of the movement and the focus direction of the user.

According to another aspect, a controller is configured to determine an access level of a user via identification information received via at least one of an authorized access interface on a remote device, a touch identification feature on a remote device, and a sensor on the remote device to determine if the user has authorized access to device information.

According to another aspect, a remote device is at least one of a handheld device having a display and a wearable device having a projector. The remote device is configured to utilize at least one of augmented reality and mixed reality to display a virtual image to a user.

According to another aspect, an information system for a medical facility in which visual identifiers are associated with the medical facility where the information system includes a query member associated with each visual identifier. The query member is at least one of a patient identification feature, a treatment device, and a room environment. A controller is configured to communicate with a remote device and a server. The controller is configured to recognize the visual identifiers sensed by the remote device, associate the visual identifiers with information related to at least one of a patient, the treatment device, and the room environment based on the query member, retrieve the information from an information source, and generate a virtual image including the information to be communicated to a user via the remote device.

According to another aspect, an information source is at least one of a local server, a remote server, a sensor assembly of a treatment device, and a caregiver interaction system.

According to another aspect, each visual identifier is coupled to at least one of a room plaque associated with a room environment, a patient identification feature associated with a patient, a treatment device, and a surface of the room environment.

According to another aspect, a controller is configured to retrieve information related to a patient from an electronic medical record stored in a server.

According to another aspect, a controller is configured to compare information with a facility protocol stored in a server. A virtual image includes at least one of the facility protocol and a prompt for action aligned with the facility protocol.

According to another aspect, a remote device is a handheld device having a display and an imager configured to capture image data within a field of detection. A controller is configured to overlay a virtual image over the image data captured by the imager to communicate the information to a user via the display.

According to another aspect, a remote device is a wearable device that includes a projector configured to project a virtual image to communicate information to a user.

According to another aspect, a wearable device includes environmental sensors configured to sense environmental information in a surrounding area and user sensors configured to sense at least one of movement and focus direction of a user. A controller is configured to update a virtual image to a subsequent virtual image in response to at least one of movement of the user and focus direction of the user.

According to another aspect, a controller is configured to determine an access level of a user based on identification information received by a remote device. Information in a virtual image is based on the access level.

According to another aspect, a method of displaying information to a caregiver includes sensing a visual identifier positioned within a field of detection of a sensor of a remote device via at least one of an imager and an environmental sensor; recognizing the visual identifier; retrieving information relating to at least one of a room environment, a patient, and a treatment device based on the configuration of the visual identifier; generating a virtual image including the information; and displaying the virtual image via at least one of a display of the remote device and within a field of view of a user of the remote device.

According to another aspect, a method includes coupling a visual identifier to at least one of a room environment, a treatment device, a patient identification feature, and a room plaque and positioning a remote device such that the visual identifier is within a field of detection.

According to another aspect, a method includes determining an access level of a user. A step of generating a virtual image includes generating the virtual image to include information according to an access level of the user.

A means for conveying information to a caregiver at a medical facility includes a means for identifying associated with a room environment of the medical facility. A means for controlling is configured to communicate with a remote device and a server. The means for controlling is configured to recognize the means of identifying sensed by the remote device, associate the means for identifying with patient information stored in the server. And generate a virtual image including the patient information to be communicated to the caregiver via a remote device.

Related applications, for example those listed herein, are fully incorporated by reference. Descriptions within the related applications are intended to contribute to the description of the information disclosed herein as may be relied upon by a person of ordinary skill in the art. Any changes between any of the related applications and the present disclosure are not intended to limit the description of the information disclosed herein, including the claims. Accordingly, the present application includes the description of the information disclosed herein as well as the description of the information in any or all of the related applications.

It will be understood by one having ordinary skill in the art that construction of the described disclosure and other components is not limited to any specific material. Other exemplary embodiments of the disclosure disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes, and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

What is claimed is:

1. An information system for displaying virtual signage in a medical facility, comprising:
   a treatment device including a sensor assembly configured to sense device information about the treatment device and patient information about a patient using the treatment device;
   a visual identifier operably coupled to the treatment device; and
   a controller configured to communicate with a remote device having a sensor for sensing the visual identifier within a field of detection, wherein the controller is configured to:
   recognize the visual identifier sensed by the remote device;
   determine device information associated with the visual identifier based on a configuration of the visual identifier;
   receive sensed device information relating to the treatment device and sensed patient information relating to the patient associated with the visual identifier from the treatment device;
   compare at least one of the sensed device and patient information with at least one of a fall risk protocol and a pulmonary risk protocol;
   generate a virtual image including the sensed device and patient information and risk information related to the at least one of the fall risk protocol and the pulmonary risk protocol configured to be viewed via the remote device;
   determine a direction of focus for eyes of a user;
   determine a field of view of the user based on the direction of focus for the eyes;
   project the virtual image as a projected virtual image via a projector into a surrounding environment within the field of view of the user;
   determine a user interaction with the projected virtual image;
   determine a selection based on the user interaction with the projected virtual image;
   project an updated projected virtual image into the surrounding environment via the projector based on a sensed user interaction with the projected virtual image; and
   adjust the treatment device in response to the selection made via the projected virtual image.

2. The information system of claim 1, wherein the treatment device is at least one of a mattress, a medical bed, a surgical table, and a vital signs monitor.

3. The information system of claim 1, wherein the controller is configured to retrieve patient information from an electronic medical record stored in a server, and wherein the virtual image includes the patient information from the electronic medical record.

4. The information system of claim 1, wherein the controller is configured to communicate with the sensor of the remote device that is configured to sense at least one of movement of the user of the remote device and the direction of focus for the eyes of the user, wherein the controller is configured to generate the updated projected virtual image in response to at least one of the movement and a change in the direction of focus for the eyes of the user.

5. The information system of claim 1, wherein the controller is configured to determine an access level of the user via identification information received via at least one of an authorized access interface on the remote device, a touch identification feature on the remote device, and the sensor on the remote device to determine if the user has authorized access to the device information.

6. The information system of claim 1, wherein the remote device is a wearable device having the projector, and wherein the remote device is configured to utilize at least one of augmented reality and mixed reality to display the virtual image to the user.

7. The information system of claim 1, wherein the remote device is a wearable remote device that includes environmental sensors configured to sense environmental information in a surrounding area and user sensors configured to sense movement of the user, wherein the controller is configured to update the virtual image to the updated projected virtual image in response to at least one of the movement of the user and a change in the direction of focus of the user.

8. The information system of claim 1, wherein the controller is configured to:
   receive at least one of call information from a nurse call system and interaction information from a caregiver interaction system; and
   generate the virtual image including at least one of the call information from the nurse call system and the interaction information from the caregiver interaction system.

9. An information system for a medical facility in which visual identifiers are associated with said medical facility, the information system comprising:
   a query member associated with each visual identifier, wherein the query member is at least one of a patient identification feature, a treatment device, and a room environment; and
   a controller configured to communicate with a remote device and a server, wherein the controller is configured to:
   receive a picture from the remote device including at least one visual identifier and a surrounding environment proximate the at least one visual identifier, the picture being image data of a real-world environment with at least one physical object in the surrounding environment;
   recognize the at least one visual identifier in the picture;
   associate the at least one visual identifier with information related to at least one of a patient, the treatment device, and the room environment based on the query member;
   retrieve the information from multiple information sources including the server and at least one of a nurse call system and a caregiver interaction system;
   generate a virtual image including the information, the information including at least one of sensed information, risk information relating to at least one facility protocol, call information from the nurse call system, and interaction information from the caregiver interaction system;
   overlay the virtual image on the image data of the picture to augment the picture and form a combined image depicting the information in the real-world environment with the at least one physical object in the surrounding environment; and
   communicate the combined image to a user via a display of the remote device.

10. The information system of claim 9, wherein the server is at least one of a local server and a remote server, and wherein the multiple information sources includes at least one of the local server, the remote server, a sensor assembly of the treatment device, and the caregiver interaction system.

11. The information system of claim 9, wherein each visual identifier is coupled to at least one of a room plaque associated with the room environment, the patient identification feature associated with the patient, the treatment device, and a surface of the room environment.

12. The information system of claim 9, wherein the controller is configured to retrieve the information related to the patient from an electronic medical record stored in the server.

13. The information system of claim 9, wherein the controller is configured to compare the information with a facility protocol stored in the server, and wherein the virtual image includes at least one of the facility protocol and a prompt for action aligned with the facility protocol.

14. The information system of claim 9, wherein the remote device is a handheld device having the display and an imager configured to capture the picture within a field of detection.

15. The information system of claim 9, wherein the controller is configured to determine an access level of the user based on identification information received by the remote device, and wherein the information in the virtual image is based on the access level.

16. The information system of claim 9, wherein the display is a display screen, and wherein the controller is configured to communicate the combined image to the display screen of the remote device as a combined augmented picture.

17. A method of displaying information to a caregiver, comprising:
sensing a visual identifier positioned within a field of detection of a sensor of a remote device via at least one of an imager and an environmental sensor;
recognizing the visual identifier;
receiving information relating to at least one of a room environment, a patient, and a treatment device based on a configuration of the visual identifier, the information including sensed data related to the treatment device and the patient;
receiving at least one of call information from a nurse call system and interaction information from a caregiver interaction system;
comparing the sensed data with facility protocols, the facility protocols including at least one of safety protocols, device protocols, and risk information;
prompting an action based on the facility protocols in response to the sensed data;
generating a virtual image including the information, the sensed data, the risk information, and at least one of the call information and the interaction information, the virtual image including the action based on the at least one of the safety protocols and the device protocols;
displaying the virtual image via at least one of a display of the remote device and within a field of view of a user of the remote device;
determining a user interaction with the virtual image;
monitoring a user position relative to the virtual image;
generating at least one of a new virtual image and an updated virtual image based on the user interaction and the user position relative to the virtual image; and
displaying the at least one of the new virtual image and the updated virtual image.

18. The method of claim 17, further comprising:
coupling the visual identifier to at least one of the room environment, the treatment device, a patient identification feature, and a room plaque; and
positioning the remote device such that the visual identifier is within the field of detection.

19. The method of claim 17, further comprising:
determining an access level of the user, wherein the step of generating the virtual image includes generating the virtual image to include the information according to the access level of the user.

20. The method of claim 17, wherein the step of displaying the virtual image includes projecting the virtual image via a projector to form a projected virtual image into a surrounding environment, and wherein the step of determining the user interaction includes determining a selection based on the user interaction with the projected virtual image, the method further comprising:
adjusting the treatment device in response to the selection made via the projected virtual image.

* * * * *